(12) United States Patent
McCarthy et al.

(10) Patent No.: US 6,904,408 B1
(45) Date of Patent: Jun. 7, 2005

(54) BIONET METHOD, SYSTEM AND PERSONALIZED WEB CONTENT MANAGER RESPONSIVE TO BROWSER VIEWERS' PSYCHOLOGICAL PREFERENCES, BEHAVIORAL RESPONSES AND PHYSIOLOGICAL STRESS INDICATORS

(76) Inventors: John McCarthy, 5950 Canoga Ave. Ste 401, Woodland Hills, CA (US) 91367; Eileen McCarthy, 5950 Canoga Ave. Ste 401, Woodland Hills, CA (US) 91367

( * ) Notice: Subject to any disclaimer, the term of this patent is extended or adjusted under 35 U.S.C. 154(b) by 812 days.

(21) Appl. No.: 09/693,677

(22) Filed: Oct. 19, 2000

(51) Int. Cl.[7] ............................................. G06F 17/60
(52) U.S. Cl. ......................................................... 705/2
(58) Field of Search ............................. 709/203; 705/2, 705/3, 4, 5, 7

(56) References Cited

U.S. PATENT DOCUMENTS 6,602,191 B2 * 8/2003 Quy ........................... 600/300

FOREIGN PATENT DOCUMENTS

JP          409276234 A   * 10/1997

OTHER PUBLICATIONS

Wireless personal area networks in telemedical environment; Publication date 2000.*

* cited by examiner

*Primary Examiner*—Pierre E. Elisca
(74) *Attorney, Agent, or Firm*—Charles R. Steffel; Thomas G. Raffin; Patent Smart P.L.L.P.

(57) ABSTRACT

A BioNet method, system and personalized web content manager responsive to browser viewers' psychological preferences, behavioral responses and physiological stress indicators for an advertising measurement and recommendation system that correlates the physiologic parameter responses to impressions of (World Wide Web and multimedia Web television) advertisements with post-impression transactional activity, clickthroughs and sales, to measure the effectiveness of the advertisements and recommend preferred media choices and media themes to media providers. The client connection with a PC browser viewer communicates via IP packets to a server. A physiologic monitor is connected to the PC by hardware means selected from the choices bi-directional parallel port, universal serial bus, serial port, firewire, infrared port, and wireless, which communicates physiologic information via Internet Protocol to a server.

9 Claims, 22 Drawing Sheets

Media impression to web browser from media providers from web server or DVS-cable TV or web phone USER BROWSER with physiologic monitor observes and transmits transaction activity, behavior and physiologic responses before during and after ad impressions PSYCHOLOGICAL SERVER analyzes and establishes PPI (correlation of media preference and sales success) and thereafter PPI suggests media choices to media providers Media impression to web
browser from media
providers from web server or
DVS-cable TV or web phone

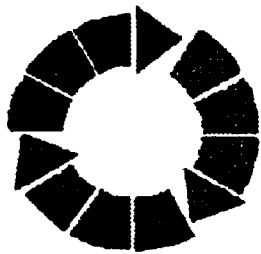

USER BROWSER with
physiologic monitor
observes and transmits
transaction activity, behavior
and physiologic responses
before during and after ad
impressions PSYCHOLOGICAL SERVER
analyzes and establishes PPI
(correlation of media
preference and sales success)
and thereafter PPI suggests
media choices to media
providers FIG. 1 BioNet Cycle of Operations

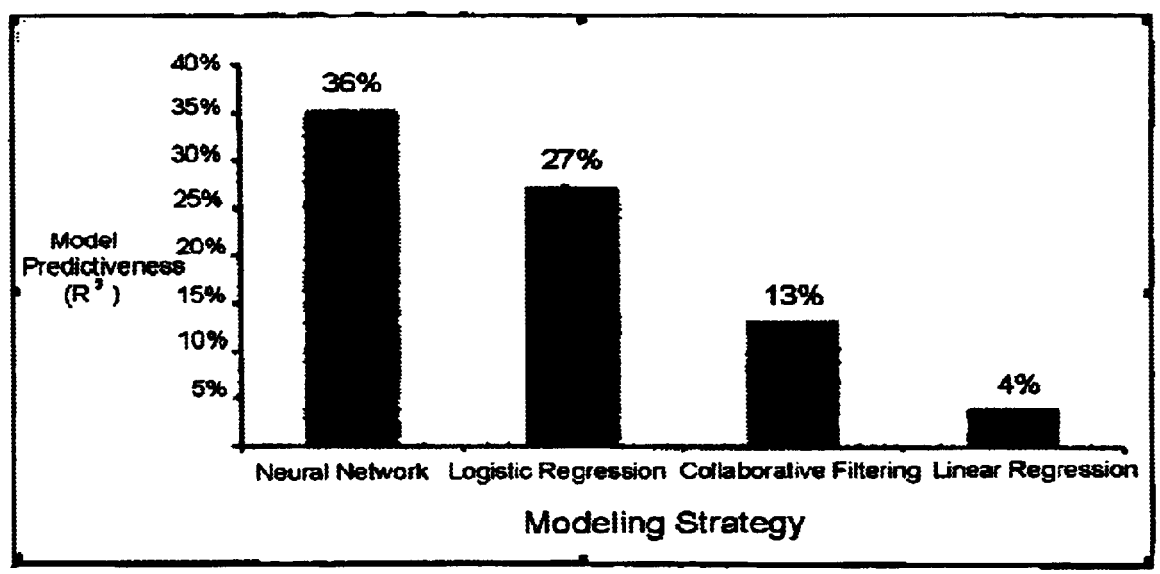
FIG. 2 PRIOR ART Comparison of modeling methods by APT Applied Predictive Technologies

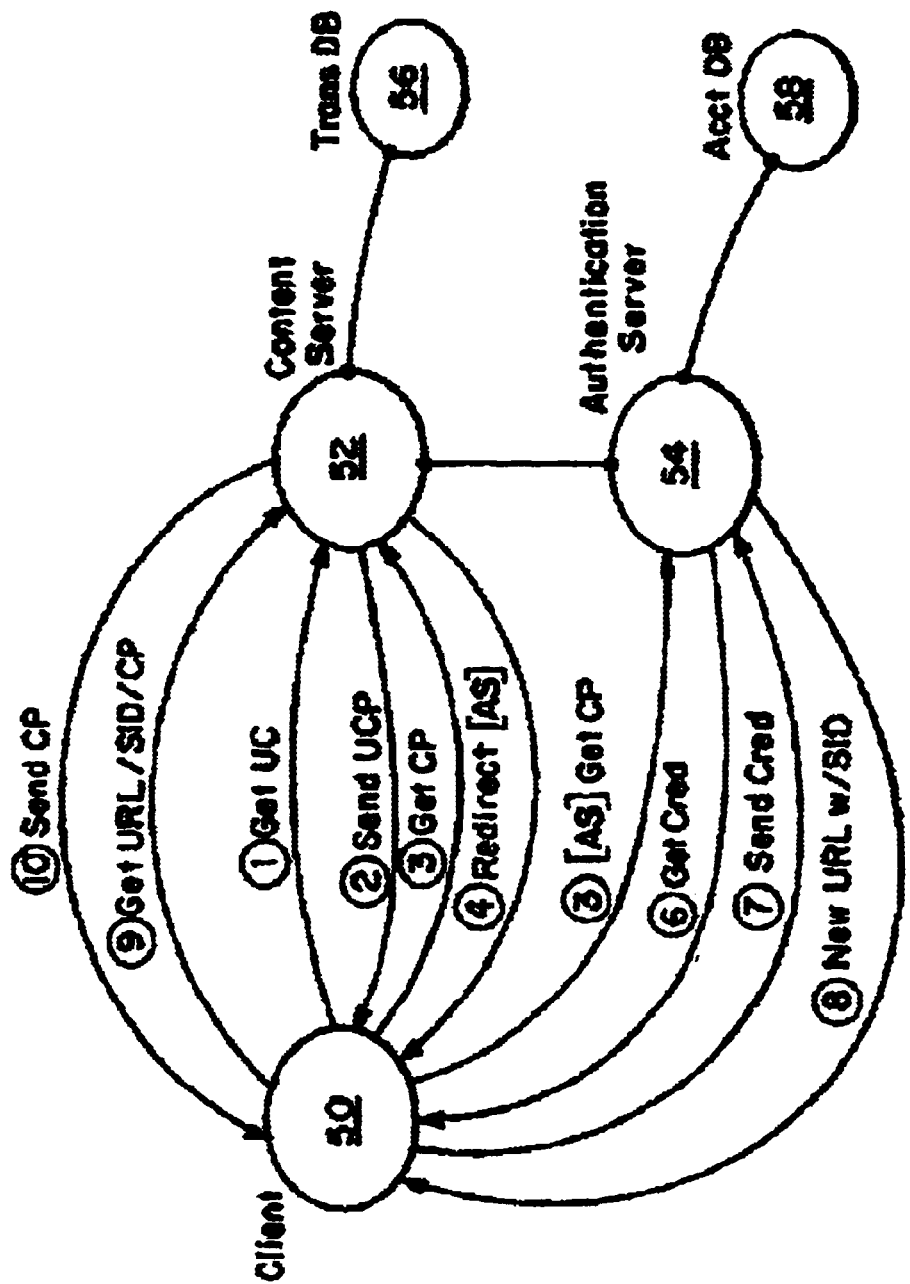
FIG. 3 PRIOR ART Client server exchange session by Levergood

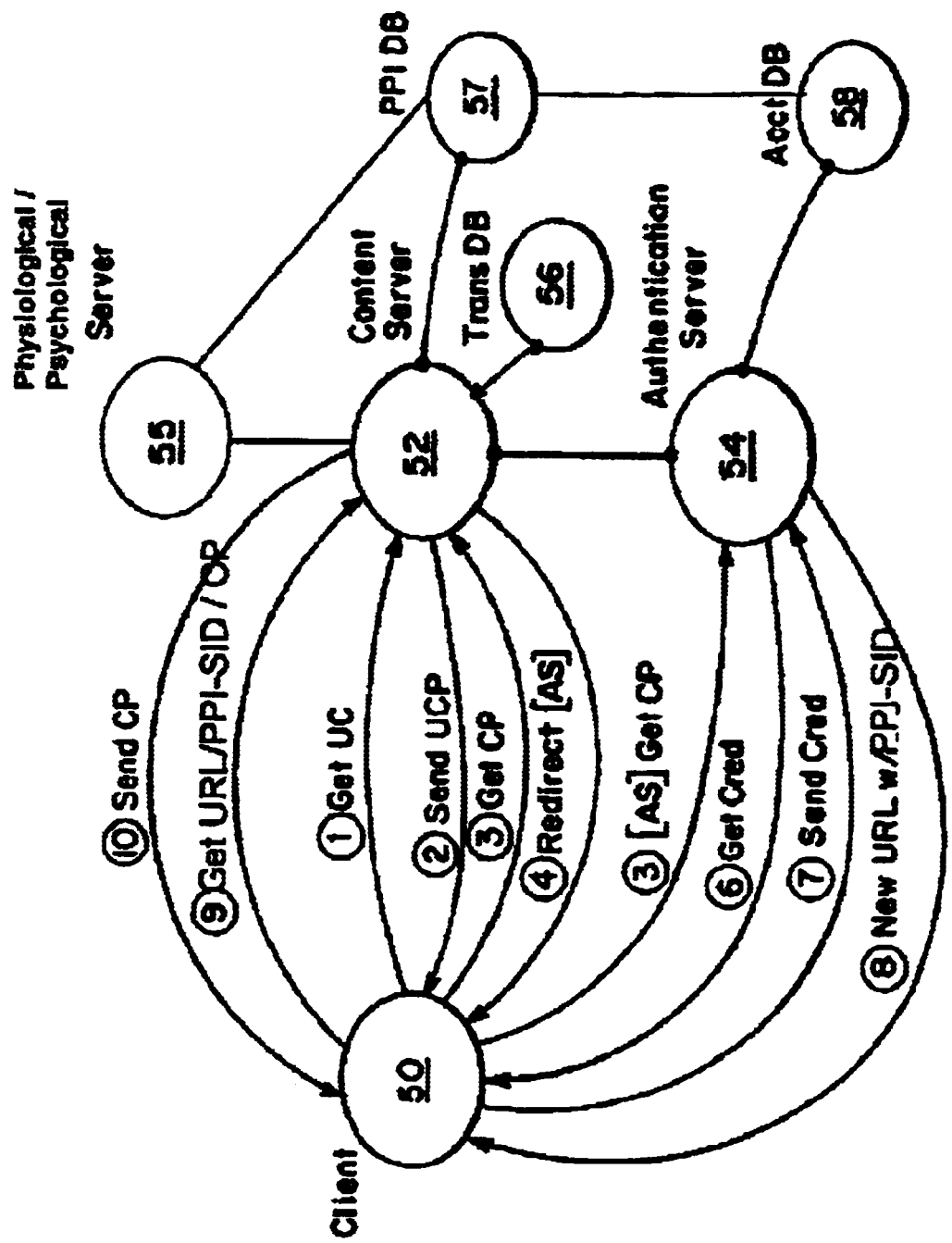
FIG. 3A   NEW

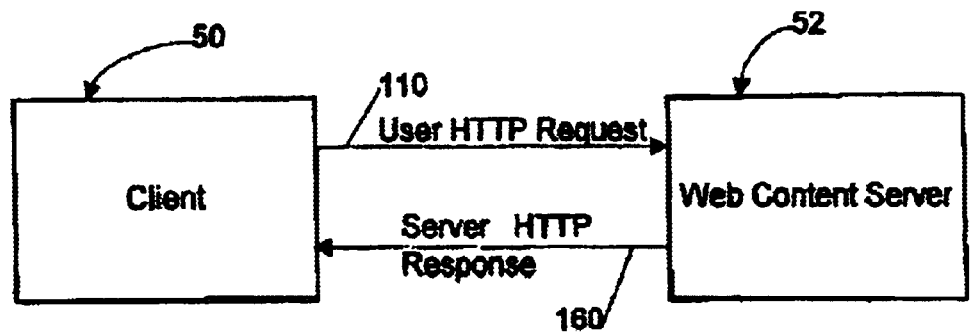
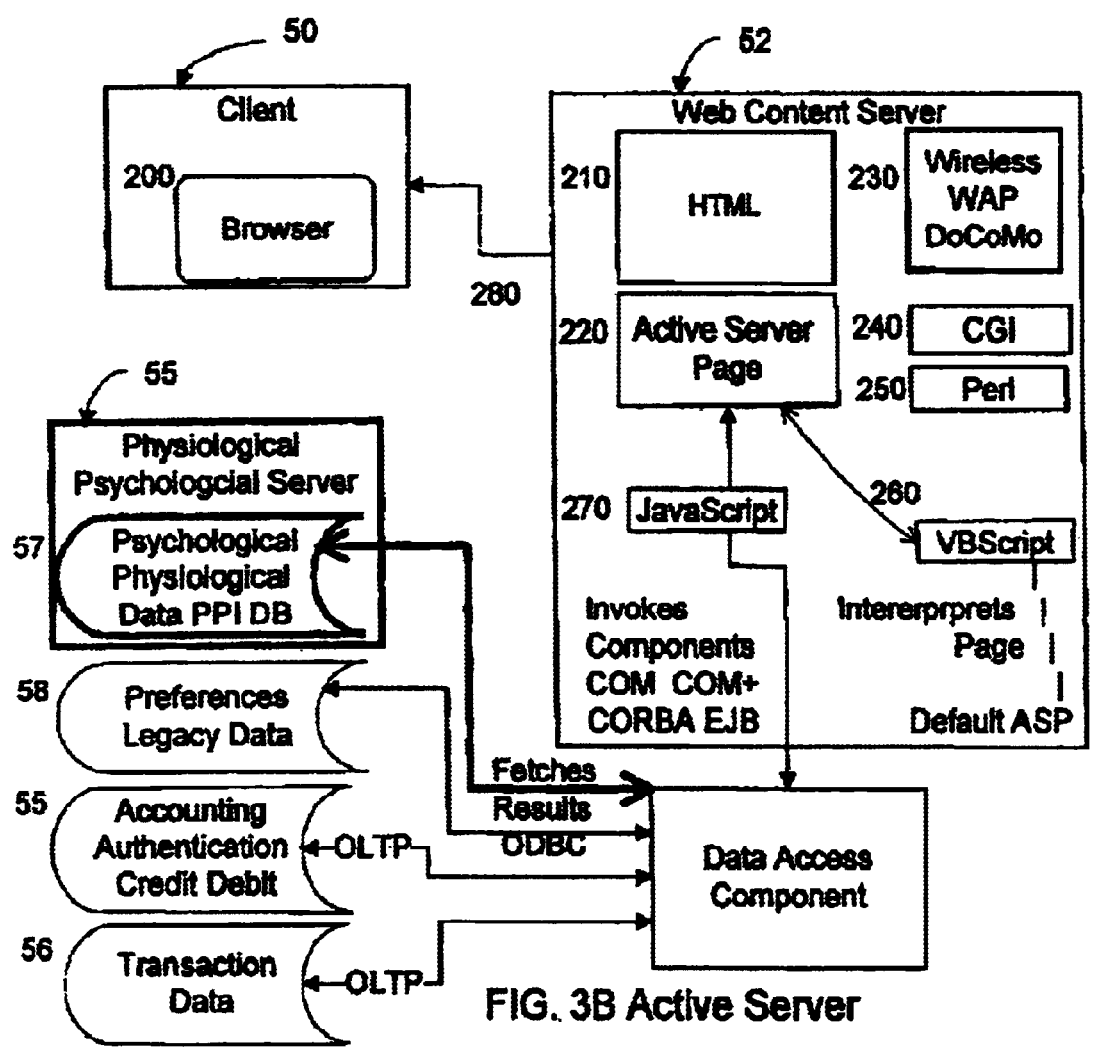
FIG. 3B Active Server

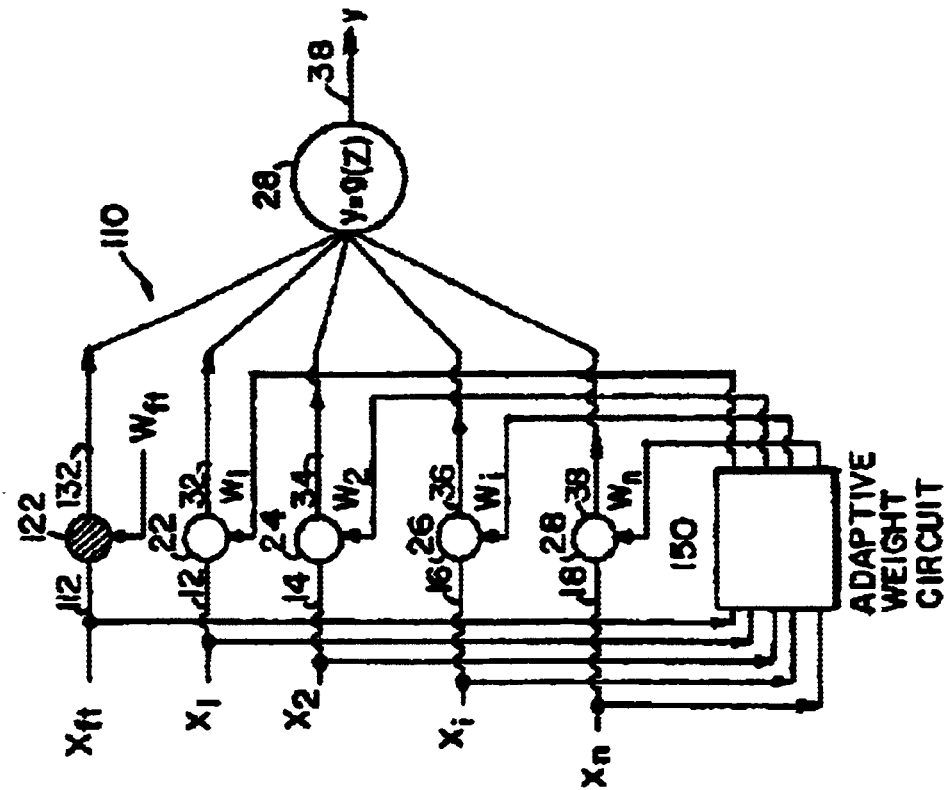
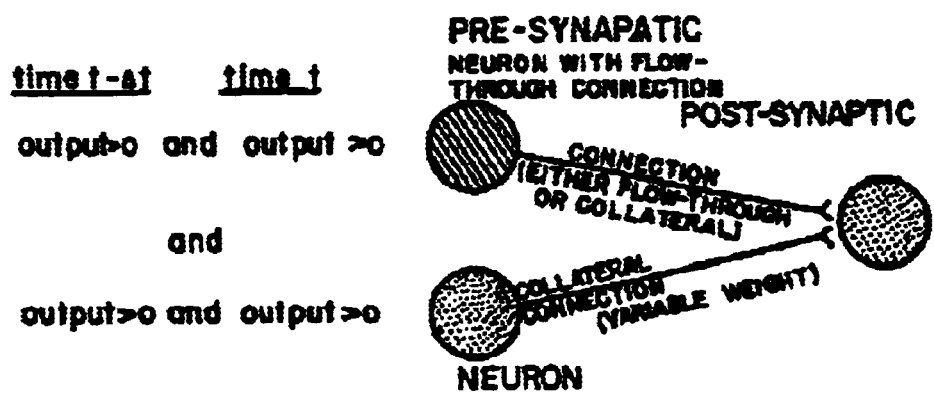
FIG. 4 Illustrates the Dynamically Stable Associative Learning Neural Network System of Alkon's first patent

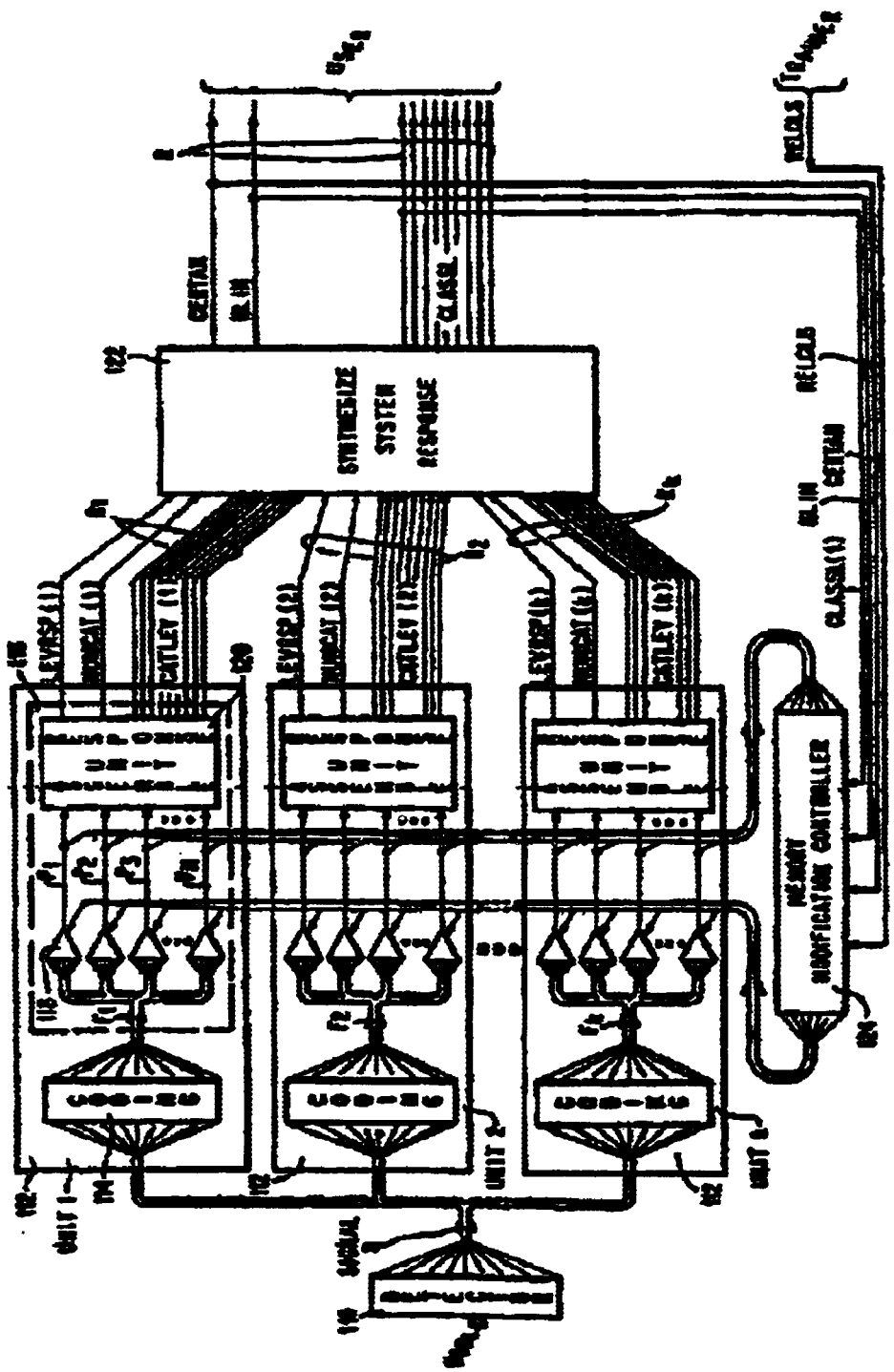
FIG. 4A PRIOR ART Cooper et al Parallel Multi-unit adaptive nonlinear pattern class separator and

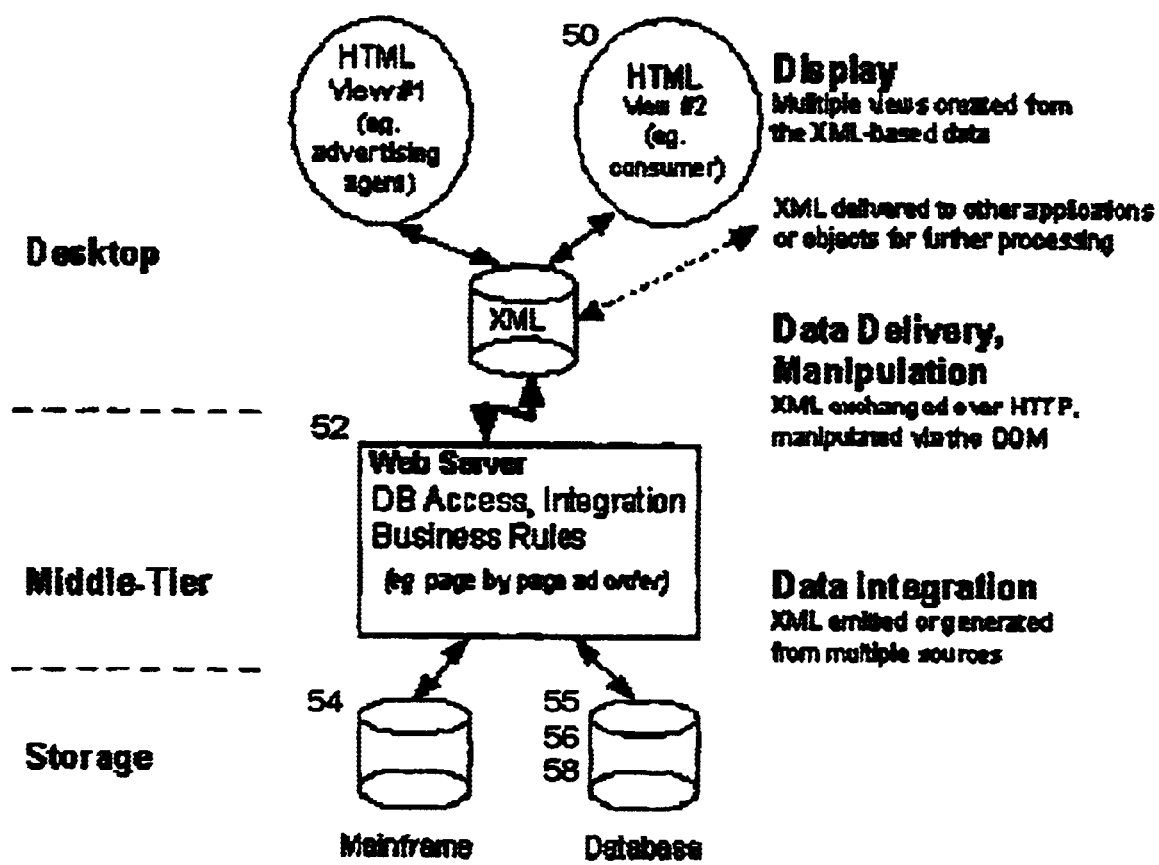
FIG. 5  A Three Tier Implementation

Bionet Database

| | A | B | C | D | E | F | G | H | I |
|---|---|---|---|---|---|---|---|---|---|
| 1 | demographic | general | biograds | medical | credit score | psycho-cogn. | buy score | Cooks data | behave data |
| 2 | race | address | skin temp | weight | credit source | ext int | pur./30 | sites hit | guilt |
| 3 | age | zipcode | pulse | height | occup."A8" | SN | pur./90 | date/time | trust |
| 4 | gender | climate | BP | BSA | educ. "A9" | thot feel | pur./180 | freq of hit | anger |
| 5 | sex preference | lifestyle | resp rate | age "A3" | net worth | JP | pur./270 | # hit/page | fear |
| 6 | # of children | household size | EMG | DOB "A15" | income | | pur./365 | sales/logon session | happiness |
| 7 | family stage | home ownership | EEG | blood type | annual savings | | category of purch | frequency | nervous |
| 8 | occupation | dwelling type | voice stress | health "A18" | collections? | | | time since last visit | generosity |
| 9 | education | # of dwell. owned | gesture recog | meds/category | judgement? | | | ratio of visit/purch | brand loyalty |
| 10 | marital status | # phones | GSR | smoke? | lawsuit? | | | site/catgry | stubborn |
| 11 | nationality | # phone lines | pupil dilation | type of tobacco | encumbrd? | | | last pg visited prior | family loyalty |
| 12 | religion | # cell ph. | eye blink | drink? | DBAs? | | | 2 pgs prior to sale | name loyalty |
| 13 | citizenship | # comp | drug/ hormone | drink type | self empl? | | | 3 pgs prior | web loyalty |
| 14 | birthplace | computer type | iris scan | drugs? | work full /part time? | | | | stubbornness |
| 15 | DOB | # PDA | fingerprint | disability | student? | | | | impatient |
| 16 | political side | # pagers | Bioaccess method | dis. type | # donat/yr | | | | skeptic |
| 17 | language | # TVs | | activity cat. | donat amnt | | | | advocate |
| 18 | health | comp con | | body type | # vac / yr | | | | finicky |
| 19 | | IP tel | | body size | debt / inc | complain | | | detailed |
| 20 | | alien res. | | chron ill. | prof. Licen. | | | | |
| 21 | | alien origin | | acute ill | avail credit | | | | |
| 22 | | # pets | | diagn / history | payment method | | | | |
| 23 | | pet type | | | | | | | |
| 24 | | hobbies | | | | | | | |
| 25 | | tel# | | | | | | | |
| 26 | | satellite video | | | | | | | |
| 27 | | cable A/V | | | | | | | |
| 28 | | modem speed | | | | | | | |
| 29 | | modem type type | | | | | | | |
| 30 | | ISP access | | | | | | | |

Fig. 8

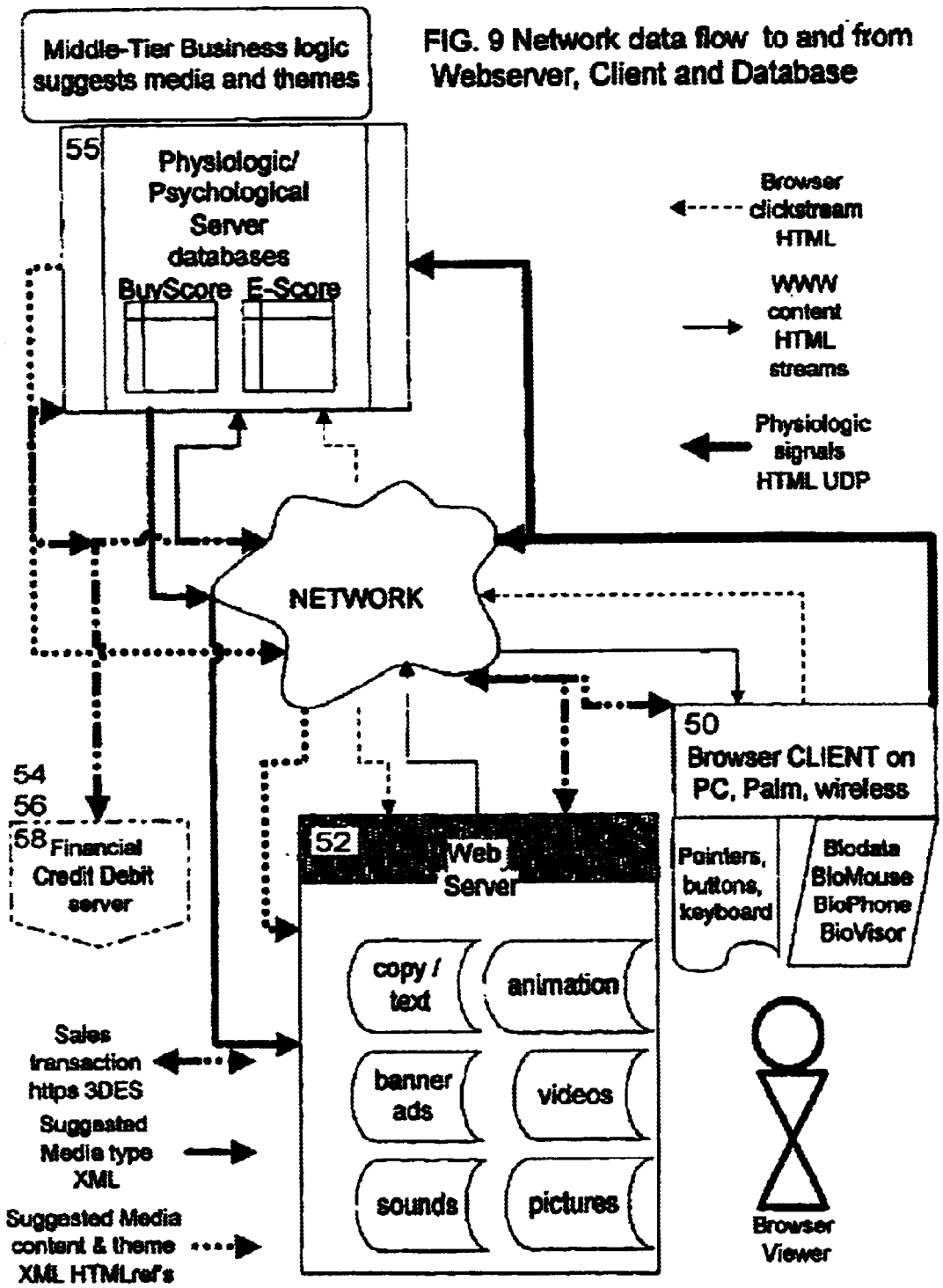

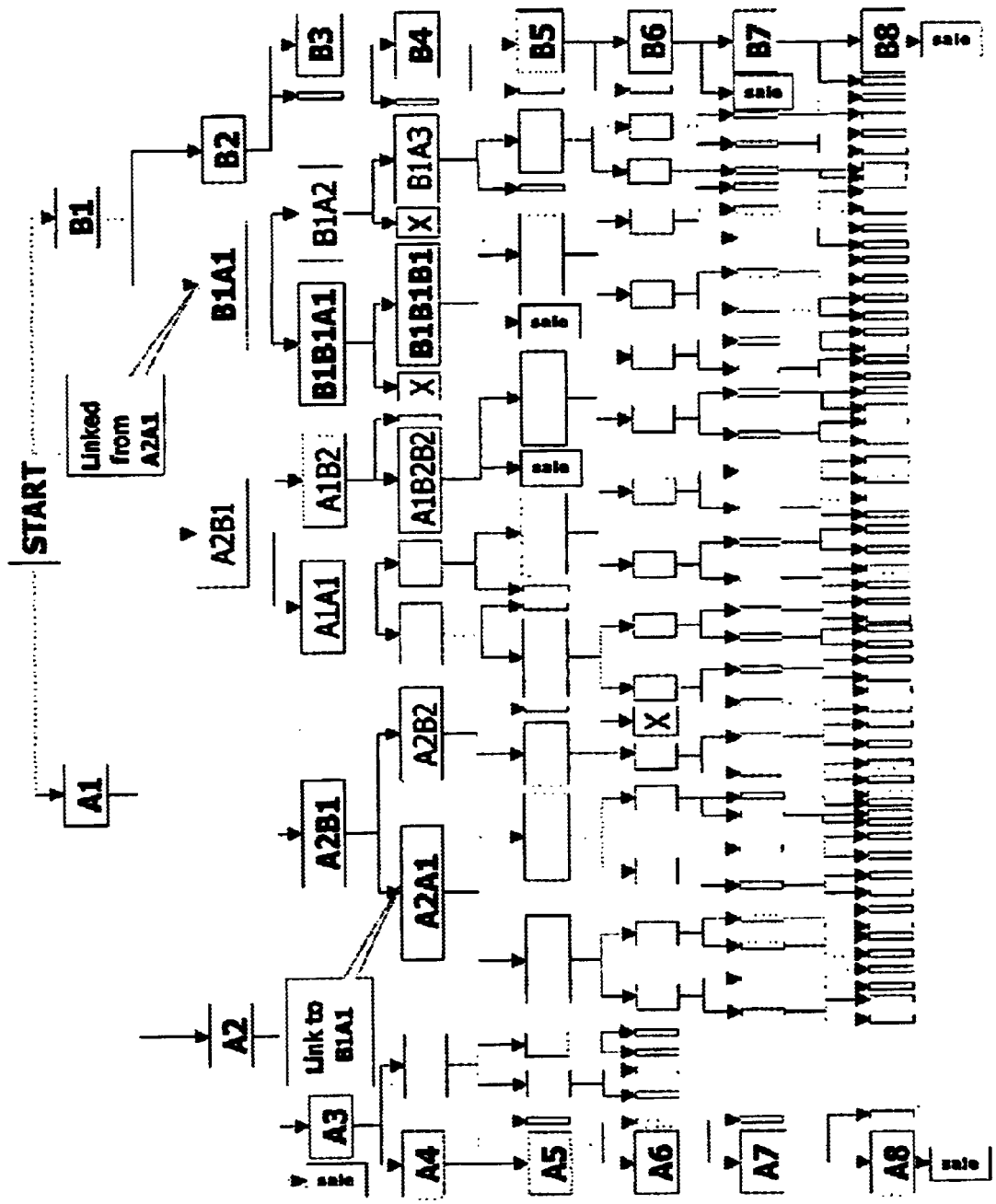
FIG. 10 Tree Diagram Footprint Pathways

Process Chart
BioMouse Operation

| | | Operate | Transport | Show | Idle |
|---|---|---|---|---|---|
| Step 1 | Obtain blood pulse / Plethysmograph O2 Sat data | xxxxxx | | xxxxxx | |
| Step 2 | Sample / Convert O2 Sat To digital serial data | xxxxxx | | | |
| Step 3 | Add to buffer to make packet | | | | xxxxxx |
| Step 4 | Obtain baseline SWEAT GSR/SCA data | xxxxxx | | xxxxxx | |
| Step 5 | Sample / Convert SWEAT GSR/SCA to digital serial data | xxxxxx | | | |
| Step 6 | Add to buffer to make packet | | | | xxxxxx |
| Step 7 | Obtain baseline fingertip temperature | xxxxxx | | xxxxxx | |
| Step 8 | Sample / Convert temperature To digital serial data | xxxxxx | | | |
| Step 9 | Add to buffer to make packet | | | | xxxxxx |
| Step 10 | Send Data Packet | | xxxxxxx | | |

FIG. 14

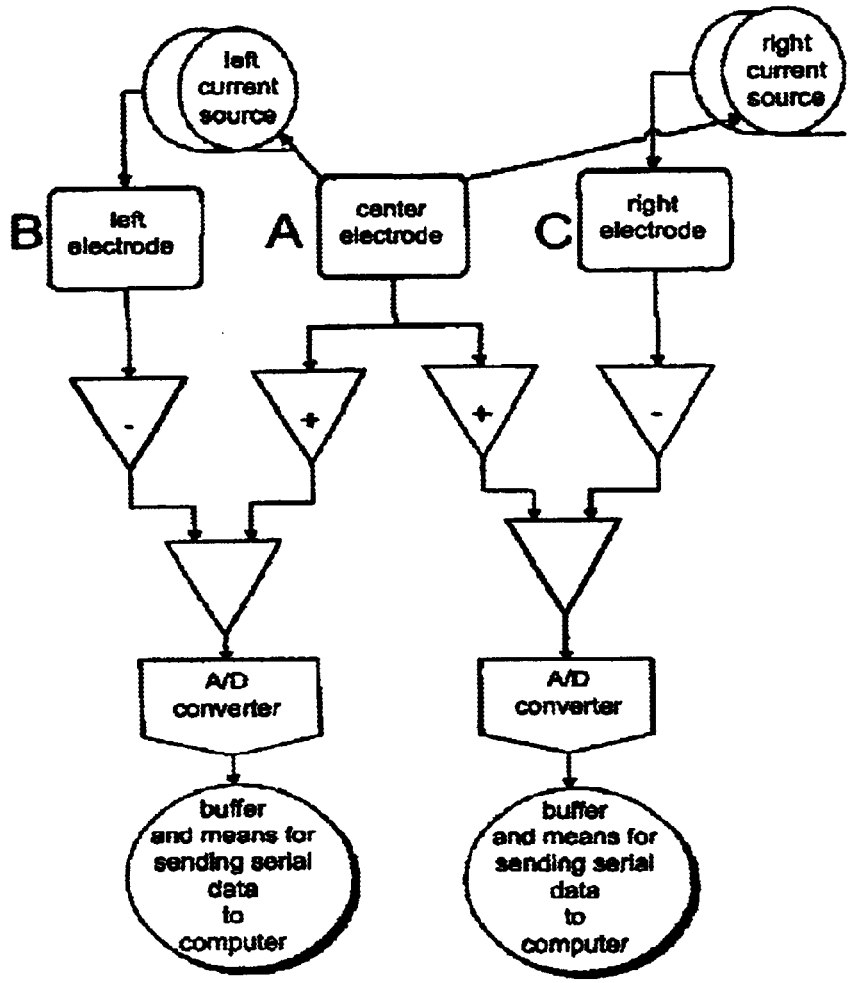

Figure 1. BioElectrode Mouse or BioMouse

Center of palm rests on a third electrode A.
Plurality of electrodes B C located on upper third of hump and symmetrical around midline.
Mouse has humped shape. Thumb rests on side of the hump on the mouse.

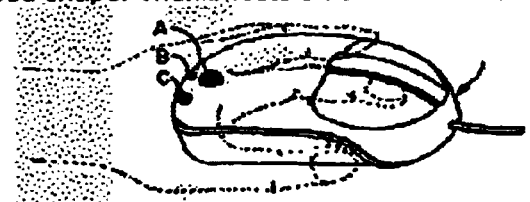

Edge of palm near the thumb rests on back of hump of mouse.
Buttons on mouse and wires or optical connection to computer are located
at opposite end of mouse from electrodes - moisture sensors.

FIG. 15 Figures 1 and 2 from US patent Application 09/497,096 which is herein incorporated by reference

BIONET METHOD, SYSTEM AND PERSONALIZED WEB CONTENT MANAGER RESPONSIVE TO BROWSER VIEWERS' PSYCHOLOGICAL PREFERENCES, BEHAVIORAL RESPONSES AND PHYSIOLOGICAL STRESS INDICATORS

BACKGROUND OF THE INVENTION

1. Field of the Invention

The present invention relates to website media content controls used to make real-time selections of media displayed to a consumer viewer of a website and methods for selecting the materials that will satisfy the viewer, meet targets of advertisers to specific audiences and induce the sale of merchandise/download pay-for-use media. More particularly, the present invention pertains to a BioNet method, system and personalized web content manager used to customize the web browsing experience of the viewer and facilitate online sales by web site merchandisers, the BioNet method and system being responsive to browser viewers' psychological preferences in a legacy database, and at least one of available real time observable behavioral signals that indicate attention and stress. The real time observable behavioral emotional indicators include skin temperature, pulse rate, heart rate, blood pulse volume, respiration rate, respiration volume, EMG electromyogram, EEG electroencephalogram, ERP evoked response potential a specialized EEG, voice stress, gesture recognition (video face tracking, eye motion, limb-hand finger point tracking, infra red jaw motion or clenching, sweat/GSR galvanic skin resistance, pupil dilation, eye blink response, drug and hormone levels via sweat chemical analyzer, which are obtained by computer accessories such as a video camera on a PC/workstation, a voice stress analyzer on a PC workstation or independent IP network vehicles, BioPhone, BioMouse, BioHeadband, BioBand, BioRemote control, 2way BioPager, BioVRVisor. BioNet method, system and personalized web content manager advances of the art of managing web content by web servers and ad servers in the field of filtering, analyzing the time series of browser users clicks called clickstream in real time using the behavioral and physiological signals as a personal signature of the browser operator creating emotional footprints or track taken toward or away from online purchases. Several heading discuss relevant prior inventions upon which the present invention depends.

Search Engines That Rank Available Material Based on Personal Likes, Dislikes and Interests have been Developed for Selection of Reading Materials and Have Become Useful Assistants for Online Purchases When the Internet was considered an information highway, search tools were needed to sort through the millions of documents available to find those that were of interest. Search engines were invented to automate the process of sorting and ranking materials by relevance. Prior art inventions relate to information retrieval include U.S. Pat. No. 5,784,608 by Meske—Hypertext information retrieval using profiles and topics relate to selection of information of interest, in which a client/server model for information retrieval of online information resources which includes the receipt of a plurality of information organized by profile and topic in a first markup language, and the parsing of the plurality of information into portions of information in a second markup language, including anchors referencing each of the portions of information to allow hypertext viewing and accessing. The Meske patent emphasized the use of SGML Standard General Markup Language as a second markup language to provide keys to selected information segments within email and news articles from the Internet, and on-line services, filtering the vast amount of information which is available in order that a user obtain that information which is of interest to the viewer.

Recent U.S. Pat. No. 6,067,539 by Cohen shows systems have evolved to intelligent information retrieval system that finds matches to request with information, scores the relative merit of the matches, and displays the matches in ranked order. Websites used for searches such as AltaVista.com, Yahoo.com, AskJeeves.com, Google.com, Lycos.com, Excite.com and others utilize automated bots that collect information and use a stored index for rapid retrieval. The search engines include typical components (a) finder/locater of sources of information, (b) a source repository for storing the locations of information; (c) a sampler for sampling messages from the located source of information; (d) a matcher for determining a matching score for the retrieved message; and (e) a message repository for storing the retrieved message and the matching score.

The personal search systems are becoming more personalized for example the U.S. Pat. No. 5,890,152 by Rapaport is a "Personal Feedback Browser For Obtaining Media Files" that uses a personal profile database obtaining media files from the internet. Selected media files are displayed based on user-specified information stored in the personal profile database, which includes, the interests, attitude/aptitude, reading comprehension and tastes of a user.

The GroupLens System was developed means to gather research data on personalized recommendation systems. The ROC collaborative filter is outlined in U.S. Pat. No. 5,842,199 to Brad Miller et al entitled "System and method and article of manufacture for using receiver operating curves to evaluate predictive utility" NetPerceptions has employed this system for several years as stated in a press release dated Nov. 15, 1996 in which they announced "'NET PERCEPTIONS SHOWCASES GROUPLENS COLLABORATIVE FILTERING TECHNOLOGY AT BIENNIAL CSCW CONFERENCE.' Net Perceptions today will be demonstrating applications of its GroupLens™ collaborative filtering technology. Net Perceptions is a corporate sponsor of the CSCW 96 conference, and will host an afternoon reception at the Hyatt Regency Cambridge from 3:30–7 p.m. on Tuesday, November 19, where new applications and technologies will be demonstrated. The GroupLens research project was first reported at CSCW 94 by the University of Minnesota team that pioneered the groundbreaking technology. The GroupLens collaborative filtering toolkit offers web marketers an affordable and flexible way to track consumer behavior and customize web contact for each consumer according to that consumer's preferences and interests."

The GroupLens system is an article recommendation system for electronic forums, specifically Usenet news. The purpose of GroupLens is to increase the value of time spent reading electronic forums. Internet newsgroups can carry hundreds of new postings every day. Many of these articles are off the newsgroup topic, and many more are not personally interesting to you. It is no longer feasible to read every article posted to a newsgroup in order to find interesting content. The GroupLens system makes reading Internet news productive again by highlighting articles of likely interest and warning against articles that will not be interesting.

In the arena of online sales a repeated visit to a website, for example a travel site, permits the web site media provider to specifically configure the site to match the interests, travel tastes (outlined by booking queries for travel at specific times to specific destinations), spending habits and credit card buying behavior (history) of the consumer. Observation of behaviors during web browsing and the resultant click through to a buy or abandonment of the web page allows implicit inferences to be made concerning the buyer's motivation and potentially selecting the customized view best suited to the consumer and even predicting future buying choices. Fore example identifying the interests and automatically sending particular marketing messages through web ads or email can make the visit more accommodating to the consumer visitor. Assuming a consistent behavior pattern exists, the web site may offer a quick response tailored to the individual desires. The site that responds becomes a sticky site that is revisited and more information is accumulated at each visit making each successive visit potentially more user friendly.

When limited individual personal information is available, the undefined interests attitudes and tastes may be matched via identification of common interests using a correlation of known variable characteristics or classification of individuals that may have associated common values. This is the so called "Group lens" or collaborative filter described in P. Resnick et al., "GroupLens: An Open Architecture for Collaborative Filtering of Netnews", reprinted from Proceedings of ACM 1999 Conference on Computer Supported Cooperative Work, pp. 175–186. Breese et al (see below) noted that where there are a large number of possible associations between variables, the large number of possibilities presents a challenge to decide which elements of the personal profile database should be used for classification of common interests. Only the strongest interests may be of useful predictive value. U.S. Pat. No. 6,018,738 to Breese et al entitled "Methods and apparatus for matching entities and for predicting an attribute of an entity based on an attribute frequency value" can use harmonized The values of the attributes may be adjusted based on number of entities that have values for a particular attribute so that the values decrease as the number increases. The attributes of the entities may be harmonized and provided with default values so that entities being matched have common attributes defined by the union of the attributes of the entities being matched. The attributes of the entities may be expanded and provided with default values so that the entities being matched have attributes that neither had originally. The match values may be normalized to provide a weight value, which may be used to predict an attribute value of a new entity, based on known attribute values of known entities. The weight values may be tuned such that relatively high weights are amplified and relatively low weights are suppressed.

In many instances, the personal buying characteristics are multi faceted and unpredictable. Personalities and behaviors are as unique and personally individualized as handwriting. Due to the similar complexity of the problem of handwritten word recognition problem, some handwriting recognition methods may be useable in observation of consumer behavior at web sites. Many pattern recognition patents focus on recognition of handwritten characters. U.S. Pat. No. 5,966, 464 to Kojima "Character recognition method and apparatus, including generation of a degree of belief" that describes a certainty factor which approximates the probability that the recognized characters are valid. The handwriting problem is similar in that the endless variation allows the complexity of the problem to increase and add new variables to be observed tracked, analyzed, and evaluated for suitability and predictive value.

The present system affords another "hard to deceive" and practically unconsciously monitored parameters which instantly indicate significant viewer responses to web media impressions.

Computer Systems with Browsers and Display Devices in Ever Smaller Packages

Prior Art FIG. 3 of U.S. Pat. No. 5,784,608 shows a standard workstation or personal computer web browser. The updated workstation with BioData input devices is shown in FIG. 7 and described in detail below in preferred embodiment is a computer system, such as a workstation, personal computer or other processing apparatus in which the client 50 operates a browser 200 or a server 150 may be operative is illustrated in FIG. 8. A web appliance browser, two way email device, minibrowser devices using WAP, wireless application protocol, new 3G wireless standard, or NTT DoCoMo Japanese standard may be a platform for a browser. A workstation in which one implementation of the present invention may be practiced includes system comprises a bus or other communication means for communicating information, and a processing means coupled with bus for processing information, a random access memory (RAM) or other volatile storage device (main memory), coupled to bus for storing information and instructions to be executed by processor. Main memory also is used for storing temporary variables or other intermediate information during execution of instructions by processor. System also comprises a read only memory (ROM) and/or other static storage device coupled to bus for storing static information and instructions for processor, and a data storage device such as a magnetic disk or optical disk and its corresponding disk drive both fixed and removable. Data storage device is coupled to bus for storing information and instructions. This may be used for storage of the various files to be described here including profiles, indices, temporary cached web information, topics, and files.

System coupled to a display device, such as a cathode ray tube (CRT) or liquid crystal display (LCD) or a VR visor to bus coupled for displaying information to a computer user. Such a display may further be coupled to bus via a frame buffer, which information such as a single or multiple frames or images for display upon display device. A keyboard alphanumeric input device, including alphanumeric and other keys, may also be coupled to bus for communicating information and command selections to processor. A voice recognition processor may take the role of the alphanumeric input device. An additional user input device is cursor control, such as a mouse, a push-pointer, a trackball, stylus, or cursor direction keys, coupled to bus for communicating direction information and command selections to processor, and for controlling cursor movement on display.

Note, also, that any or all of the components of system and associated hardware may be used in various embodiments, however, it can be appreciated that any configuration of the system may be used for various purposes according to the particular implementation. The components described above may be implemented on a device of a very small size by building a system on a chip (SOC) that incorporates microcircuits which perform the functions of the building blocks through construction of a single chip built with components which use IP intellectual property modules that allow construction of various memory processor and data transfer components as constructed with custom application specific integrated circuits ASIC's and DSP digital signal processing modules. Bio Remote control 340, BioPhone wireless 341, and 2way BioPager 342 and BioPalm Pocket PC are self contained wireless devices include within a system on a chip or miniature system with the RAM ROM CPU and Mass storage as well as BioData sensors and device controls and minibrowser displays and sometimes audio speakers or headphones. In particular FIG. 7 shows the evolution of smaller and smaller portable devices for web browsing including BioRemote controls for interactive TV, WebTV and set top cable or satellite receiver boxes 340, PDA's personal digital assistants with wireless modem communication Palm Pilot® (device from 3Com and Pocket PC 343, 2 way pagers with email and biosensors 342, cellular telephones that incorporate small lower resolution displays, DSP digital signal processors and very low-power microprocessors and biosensors such as the BioPhone wireless 343.

One skilled in the art appreciates that the following methods and apparatus may be implemented in special purpose hardware devices, such as discrete logic devices, large scale integrated circuits (LSI's), application-specific integrated circuits (ASIC's), or other specialized hardware. Other programming languages, C, BasicC, C++ and other Operating systems such as Unix, Posix, and variations of Linux platforms.

Personalization and Customization of the Web Browser Helps to get the Consumer Buyer What she or he Wants to Buy and Helps Sellers to Sell by Understanding What Motivates Buyers to Buy Boston Consulting Group has reported that eMarketplaces will increase competitive pressures on online sellers as buyers are increasingly able to comparison shop. Twenty-five percent of sellers surveyed had already decreased prices due incremental price pressures as their customers went online. By 2004, another 50% expected to also decrease their prices. In response to this threat (referred to by BCG as "commoditization"), sellers intend to cut costs, increase differentiation or both. The customization or personalization of web content is the most effective way to offer the consumer exactly what they want.

The process of getting the consumer what she or he wants must offer explicit value for the customer and requires the steps of the vendor gathering data about the customer, converting the information to differentiate customers and then customizing each offer, communication and interaction to offer explicit value for customers and in so doing meeting the vendor's objectives of building customer value while retaining revenue, profitability and customer satisfaction and loyalty.

The messages intended to reach a consumer may be very different with distinct executions for different types of consumers. For example Eddie Bauer has identified the "Help me choose" consumer who is too busy to shop and requires values and themes which focus on convenience, durability and practicality, size availability help to made expedient, you deserve something attitude and a solution oriented program. In contrast, the "Spice up your wardrobe" approach focuses on professional shoppers and provides upscale themes that include updates styles of classic look, options to spice up wardrobe, national brand trusted for quality, a fun attitude, orientation toward spontaneity. It is helpful to categorize shoppers into these profiles based on preferences explicitly given by consumers and by inference from consumer behavior.

Broadvision and Macromedia LikeMinds Personalization Server and Vignette encourage visitors to become repeat customers by offering a Web site that interacts with visitors individually and in real time, and quickly directs visitors to personally relevant content and products they are likely to purchase. The software is added to an existing web server or to a distributed server environment where media content is controlled by the LikeMinds Server. Macromedia Like-Minds enables you to meet these challenges by delivering highly-accurate product recommendations, personally relevant content, and targeted promotions for each individual Web visitor. The Macromedia's Like Minds system requires hardware platform, web server and database software. Typical systems include a Wintel ("Windows and Intel") Platform Windows NT® Server 4.0, Dual Pentium® processor, 1 GB RAM, 1 GB Hard Disk real time or a Sun Platforms Solaris 2.6, 2.7, Dual UltraSPARC-II, 1 GB RAM, 1 GB Hard Disk a Web Server such as Microsoft Internet Information Server (Active Server Pages), Netscape Enterprise Server (Live Wire), Any JSP-compliant Web server, or Any CGI-compliant Web server with Other Interfaces including COM, C, C++, Java and a Database Server Oracle 8 and 8i (native), SQL Server 7.0.

A Personal Interactive Selling System for Reducing the Sales Assistance Provided by Live Personnel has been Introduced and Patented SAS e-Intelligence indicated the objective is to build customer value revenue profitability and satisfaction. SAS has made the well known point "The more product complexity increases, the more guided selling is necessary for e-commerce success" in a online slide presentation shown in FIG. 3C.

Neural Network Systems have Optimized the Personalization of Websites and Identification of Consumer Subgroups Particularly Identifying the Subgroup that Engages in Online Fraud Human-like learning through neural networks can provide better even better results. When multiple neural networks are paralleled into one architecture such as Nestor Learning Systems (http://www.nestor.com/) generalize and discriminate among consumer groups. Differentiation is important to help eliminate consumer credit card fraud by recognizing behavior that fits a profile of a potentially fraudulent transaction. A recent article sidebar entitled "Most fraud detection tools command a hefty price, but that's starting to change" Dec. 13, 1999 PC Week (now called E-week) feature article "Strategies—Cutting Out e-fraud" described three solutions. Internet Fraud Screen from CyberSource, a 1997 a spinoff from Beyond.com, a SAS customer, uses artificial intelligence and advanced mathematics to compare new transactions with characteristics of millions of transactions in a database and assign a risk factor to each transaction. HNC Software's eFalcon uses neural network technology to ferret out fraudulent transactions. Clear Commerce Corp's Fraud-Shield released a fraud detection system. Nestor Inc released Prism to detect fraudulent online transactions that is based on neural networks. Characteristics that fit a profile of a potentially fraudulent transaction are for example a combination of the use of PO Box as a mailing address, the use of a free non-traceable email box like Juno or HotMail as a mailing address, a non working telephone number, and the delivery of high cost credit card purchases to an address that is not the same as the credit card billing address. These transactions are double checked before shipment of goods occurs.

Multimedia Type Preferences for Animation Rich Media and Chat Vary from Consumer to Consumer and Vary with the Type of Browser that is Available Less than 20% e-retailers are using web technologies such as Java, Flash, or chat functions to enhance the sales experience, according to a recent Jupiter Communications survey (August 2000 reported in eMarketer). Jupiter also reported that 60% of merchants based upgrading user-interface technologies on customer feedback. However, surveying consumers, Jupiter found that more than 50% of shoppers would use such rich media technologies. Specifically, 56% would use virtual dressing rooms and 51% would use zoom-and-spin technologies.

The dynamic nature of web interfaces presents big challenges. Some web-based media types are interactive and send new output to the user interface in discrete blocks, in response to user input or messages from the web server; others (such as animated graphics) continuously change their output without requiring any external stimulus. Moreover, the appearance of a web page is determined by the browser and modified by options set on the user's browser (e.g. a user can instruct the browser not to display graphics nor do WAP Wireless Application Protocol connected internet devices such as two way pagers and internet ready cell phones which have no high pixel density graphics display). Personalized interfaces mean that different users may interact with the web page differently on quite different user interfaces but the website delivers highly-accurate product recommendations, personally relevant content, and targeted promotions for each individual Web visitor.

For the foregoing reasons and critical limitation of the displays, wireless mobile systems will require the use of much focused ads with a concise messages. Research by Ovum <http://www.ovum.com/> discussed mobile advertising and its differences from Web marketing. Ovum advised potential mobile advertisers to use a highly targeted, low-volume, high-value model where users have a strong element of control over the number, type, and timing of ads received. Data privacy concerns regarding releasing cell phone numbers and list of services desired to marketers makes users' cooperation in accepting advertising critical. This means the advertising must support services that are vulnerable to changes by users on an ongoing basis to users, and it will require a trading-off compromised privacy for convenience.

None of these preferences uses continuous Biosignal feedback to confirm the successful match of content with suggestion that is no systems determines whether suggested content based a viewer's demographic and or psychological profile and collaborative filter is what the viewer desires. A null hypothesis test is performed whenever media is presented. The present system includes a monitored physiologic response that is used as feedback and combined with demographic/psychological background information and behavioral history to determine the unconscious of subliminal viewer responses. The unconscious stress indicators can be use with a null hypothesis test to determine if the material is stress inducing. The null hypothesis is more stress is more interest, that is less boredom. When interest is aroused, it is more likely to produce the desired result, a sale. The presence or absence of stress alone is not an indicator of interest or possibility of future purchases. Stress must be evaluated in context through neural network analysis of the whole situation

Dimensional Database Storage in Tables that Allow View and Analysis of Time Associated Data A dimensional database may be implemented using a conventional relational database program such as the Oracle8.1 product commercially available from Oracle Corporation of Redwood Shores, Calif. or the Microsoft Access and SQL7 products commercially available from Microsoft Corporation of Redmond, Wash. Virtual databases may also be used, treating several databases as if they were a single database. Conventional relational databases with specialized tools for On-Line Analytical Processing, or OLAP-optimized databases may also be used. Such databases are sometimes referred to as MOLAP, ROLAP or DOLAP databases and are described at http://www.sentrytech.com/dw05dem.htm. Non-database implementations such as those storing data using objects, records, arrays or flat files may be used to implement dimensional databases. Keys may be implemented using conventional pointers or look-up table approaches.

Method for physically storing temporal data are well known and newer developments U.S. Pat. No. 6,003,024 to Bair—Amazon.com shows a System and method for selecting rows from dimensional databases as those databases are expanded with more data associated with time in a manner that creates yet another table that allows searching for data rows that are collected over a time series Temporal query primitive functions may then be applied to the dimension tables in a manner that permits comparison of events and data that changes over time. Of particular interest in this patent is the activity of a person viewing media, typically a files or pages on a website and the sequence of files viewed and actions performed that leads toward a purchase of a product or service.

Methods for Acquiring Psychological and Physiological Information from a Web Browser Viewer Well-known tools such as the Myers Briggs personality test and the Kersey temperament sorter. The Jungian personality profile has been combined with speech analysis for purposes of "lie detection" in a personal computer system described in U.S. Pat. No. 6,006,188 to Bogdashevsky. Heretofore, systems of this type have not yet been implemented on line for entertainment or sales purposes.

Guided Selling Systems that Automate and Improve the Online Sales Process with Human-Like Interactions U.S. Pat. No. 6,070,149 by Tavor describes a virtual sales representative for assisting a customer in the selection of a purchase product from an e-shop virtual shop, and more particularly, to software which is capable of assisting a computer user to complete an on-line sales transaction in a substantially similar manner as a human sales representative, providing advice and interacting in a conversation like fashion with the browser. The automatic sales agents evolved from interactive tools used to sell mortgages by BrightStreet.

Broadband Systems that Allow Multiple Communications Channels to Reach the Home and Provide Information Selected to Match User Profile According to User's Priority and Available Bandwidth, Capability for Various Types of Messaging, Media Graphics, Streaming Media, High Quality Sound U.S. Pat. No. 6,044,403 by Gerszberg of AT&T shows a Network server platform for internet, JAVA server and video application server that enables high speed internet connections through two wire high speed copper wire connections over the existing single twisted pair using xDSL transmission schemes and coupled to a network server to provide a vast array of new services to customers. Network servers including a relaying host an intelligent services director (ISD) at the customer services equipment and a facilities management platform (FMP) at the local office allows new services such as simultaneous, multiple calls (voice analog or digital), facsimile, Internet traffic connectivity, videophone, utility metering, broadcasting, multicasting, bill viewing, information pushing in response to a user profile, directory look-up and other services that can be implemented via a network server platform via this architecture. A network server platform for hosting a plurality of services comprises, for example, a memory for storing a user profile, the user profile containing interests of a user, and for storing information related to their interests and a controller for controlling the collection of information from information servers and for pushing the collected information to the user in accordance with their defined priority.

2. Definitions of Terms and Background

Ad: For web advertising, an ad is usually a banner, a graphic image of a designated pixel, size and byte size limit. It is usually an animated GIF (a series of pictures displayed in a repetition that appears to move). Banners and other special advertising that include an interactive element, a high quality audio or visual element beyond the usual are known as rich media. Multiple locations on a given page may be available for ads.

Ad Media type: The medium for the ad, be it HTML text with tags that control characteristics (color size font design and table layout), small photos and art (GIF Graphic Interchange Format), banner ad, higher quality larger photographs (.jpg Joint Photographic Expert Group), simple audio (.wav) or synthesized music, streaming media audio (QuickTime™, REAL™ Audio or Windows™ Media Player).

Ad rotation: Ads are often rotated into ad spaces from a list. This is usually done automatically by software on the web site or at a central site administered by an ad broker or server facility that it sells impressions and sponsorships and tracks impressions for a network of web sites.

Ad space: An ad space is a sellable space on a web page that is reserved for ads. A group of spaces within a web site that share the same characteristics can be sold as an ad space group so that an ad purchase can be made for the group of spaces.

Ad view: An ad view is the same as an ad impression, that is a usually a full view single ad that appears "above the fold" on a web page when the page arrives at the viewer's display. A web page may offer space for a number of different ad views banners sidebars and pop ups.

Affiliate marketing: Affiliate marketing is the use by a web site that sells products of other web sites, called affiliates, to help market the products. The relationship implies that web sites pay commissions on sales made Amazon.com, the bookseller, created the first affiliate program and hundreds of other companies have followed since.

Banner: A banner is an advertisement in the form of a graphic image that is located across a top of a web page or is positioned in a margin or other space reserved for ads. Banner ads are usually GIF Graphics Interchange Format images that load quickly. Size limits on the file are made so that the ad file will display quickly. Most ads are animated GIF's since animation has been shown be attractive to users. Size ranges form 1 or 3 k to 70 or 90 k for animated GIF's. Most banners are 468 pixels wide by 60 pixels high. Smaller sizes include 125 by 125 and 120 by 90 pixels. Banner sizes have been established as standard sizes by the Internet Advertising Bureau (IAB).

Beyond the banner: Besides banner ads other ways to use the Internet to communicate a marketing message include: sponsoring a web site or a feature on it; e-mail newsletter ads; co-branding sharing (logo displays) with another company and its web site; contest promotion and other new ways to engage and interact with the desired audience. "Beyond the banner" may be a media rich banner, splash pages (interstitials that show up in a new browser windlow) and streaming video infomercials.

Browser: A browser is an application program that provides a way to look at and interact with all the information on the World Wide Web. The word "browser" seems to have originated prior to the Web as a generic term for user interfaces that let you browse text files online. The first Web browser with a graphical user interface was invented (Mosaic, in 1992), the term seemed to apply to Web content, too. Technically, a Web browser is a client program that uses the Hypertext Transfer Protocol (HTTP) to make requests of Web servers throughout the Internet on behalf of the browser user. Parts of Mosaic went into the first widely used browser, Netscape Navigator, and Microsoft Internet Explorer. With a few exceptions such as Opera, these Navigator and Internet Explorer browsers are the only two browsers that the vast majority of Internet users have today. Online services, such as America Online, CompuServe, and Prodigy, had their own browsers, but now offer the customized versions of Netscape (Mozilla) or Microsoft browser. The newer version of these two browsers have the ability to run applet programs in Java™ or Active X extensions to HTML.

Caching: To speed up viewing and save bandwidth, a users browser with an internal cache, network cache servers and proxy servers save recently viewed files to avoid having to resend files before each view. Using a cache of pages in a cache server or the user's computer means that some ad views won't be known by the ad counting programs and is a source of concern. Although preventing caching gives a more accurate count, specifying no caching for all pages means that users will have slower time to view from each click.

Click: is an action that requests the view of a web page. According to ad industry recommended guidelines from FAST, a click is "when a visitor interacts with an advertisement." This does not apparently mean simply interacting with a rich media ad, but actually clicking on it so that the visitor is headed toward the advertiser's destination. (It also does not mean that the visitor actually waits to fully arrive at the destination, but just that the visitor started going there.)

Click stream: A click stream is a recorded path of the pages a user requested in going through one or more web sites. Click stream information helps web site owners understand how visitors are using their site and which pages are viewed the most. Advertisers learn how users get to the client's pages, what pages they look at, and how they go about ordering a product. This is the most important behavioral record available for use in determining a user profile.

Clickthrough: A clickthrough is what is counted by the sponsoring site as a result of an ad click. In practice, click and clickthrough tend to be used interchangeably. A clickthrough, however, seems to imply that the user actually received the page instead of request only. Some advertisers are willing to pay only for clickthroughs rather than for ad impressions Click rate: Often called CTR or clickthrough rate, click rate is the percentage of ad views that resulted in clickthroughs. A clickthrough is an indication of the ad's effectiveness and it results in the viewer getting to the advertiser's web site where other messages can be provided. A click to an immediate product order window can lead to a quick sale. Evaluation of clickthrough based on the campaign objectives, how enticing the banner message is, how explicit the message is (a teaser message is more likely to be clicked), audience/message matching, how new the banner is, how often it is displayed to that particular user. Reports n general, show click rates for high-repeat, branding banners vary from 0.15 to 1%. Ads with provocative, mysterious, or other compelling content can induce click rates ranging from 1 to 5% and sometimes higher. The click rate for any given ad tends to shrink upon repetition.

Cookie: A cookie is a file on a web user's hard drive (it's kept in one of the subdirectories under the browser file directory) that is used by web sites to record data about the user. Multiple cookies may come from the same website. There may be a cookie that is associated with a specific individual session. Cookies help control multiple ad sequences by telling the web page server which ad the user has just seen so that a different ad will be rotated into the next page view.

Cost-per-action: (CPA) Cost-per-action is what an advertiser pays for each visitor that takes some specifically defined action in response to an ad beyond simply clicking on it. For example, a visitor might visit an advertiser's site and request to be subscriber to their newsletter.

Cost-per-lead: This is a yield figure for cost-per-action. Statistics can account for visitors that provide enough information to be used as a sales lead. This overall figure can be estimated regardless of how the ad is purchased. It may include other promotional costs giveaways raffle costs free subscriptions and others.

Cost-per-sale (CPS): Sites that sell products directly from their web site or can otherwise determine sales generated as the result of an advertising sales lead can calculate the cost-per-sale of web advertising.

Coulomb network: Relaxation Model for Memory with High Storage Density by Charles M. Bachmann et al.— Neural Networks, pp. 1–9. a neural network system is considered in which memories of events have already been recorded in a layer of cells. A method is found for the consolidation of the number of memories required to correctly represent the pattern environment in N dimensions using an expansion and contraction of areas. Refer to U.S. Pat. No. 4,897,811 by Scofield, entitled N-dimensional coulomb neural network that provides for cumulative learning of internal representations. This is one of several methods useable for reducing the complexity of the neural network to a minimal cumber of neural circuits necessary so that the network can operate more rapidly.

CPM: CPM is "cost per thousand" ad impressions, an industry standard measure for selling ads on web sites. This measure is taken from print advertising.

CPTM: CPTM is "cost per thousand targeted" ad impressions, apparently implying that the audience you're selling is targeted to particular demographics.

Demographics: Demographics are data about the size and characteristics of a population or audience (including for example., gender, age group, income group, purchasing history, personal preferences, and so forth).

Domain Name: A domain name locates an organization or other entity on the Internet. For example, the domain name for instance <www.totalbaseball.com> locates an Internet address for "totalbaseball.com" at Internet point 199.0.0.2 (the and a particular host server named "www". The "com" part of the domain name reflects the purpose of the organization or entity (in this example, "commercial") and is called the top-level domain name. The "totalbaseball" part of the domain name defines the organization or entity and together with the top-level is called the second-level domain name. The second-level domain name maps to and can be thought of as the "readable" version of the Internet address. See <http://whatis.com/WhatIs_Definition_Page/0,4152,211987,00.html> for the source of this definition The principal domain name standards are RFC 1034— Domain Names Concepts and Facilities available at <ftp://ftp.isi.edu/in-notes/rfc1034.txt> and RFC 1035—Domain Names Implementation and Specification <ftp://ftp.isi.edu/in-notes/rfc1035.txt>.

FAST:FAST is a coalition of the Internet Advertising Bureau (IAB), the ANA, and the ARF that has recommended or is working on guidelines for consumer privacy, ad models and creative formats, audience and ad impression measurement, and a standard reporting template together with a standard insertion order. FAST originated with Proctor and Gamble's Future of Advertising Stakeholders Summit in August, 1998. FAST's first guideline, available in March 1999, was a guideline on "Basic Advertising Measures."

Filtering: Filtering is the immediate analysis by a program of a user (click) request to determine which ad(s) to return in the requested page. A web page request combined with information using the user viewer's cookie files, IP address, login id and using a marketing database can by identify a an individual or a member of a cluster of users that can tell a web site or its ad server whether it fits a certain characteristic such as coming transferring from a particular company's address or that the user is using a particular level of browser with versions with Java, ActiveX, multimedia plug-ins or advanced HTML. The web ad server can respond accordingly.

Fold: "Above the fold," a term taken from print media for a prime viewable ad. This means an ad that is viewable as a whole as soon as the web page arrives. You don't have to scroll (down or sideways) to see it. Since screen resolution can affect what is immediately viewable, it's good to know whether the web site's audience tends to set their resolution at 640 by 480 pixels or at 800 by 600 (or higher).

Gesture recognition: Gesture recognition is the ability to interpret simple hand-written symbols such as check marks and slashes, the ability to recognize hand signals, the ability to recognize body movements of limbs and the ability to recognize eye blinks, and head/face movements. In 1998, Toshiba introduced a device that uses infrared light reflected from a user's hand to sense its motion. Computer analysis of monocular cameras (without reflector tags that were once required) to follow trace motions of body parts (waving arms) using Hidden Markov Models. Live demonstrations from Microsoft Research in Silicon Valley demonstrated 9 months ago at the Windows 2000 product release that computers are able to recognize facial components and key recognizable features on faces including mouth lines, cheek lines, lines between the eyes, eyebrow positions, nose and jaw directions all of which can indicate the direction a person is facing and head nods or shaking indicated by changes in direction of the head. A sequence of image frames can be reduces a wire frame or stick figure representation for identified facial components on each frame. In U.S. Pat. No. 6,072,494 entitled Method and apparatus for real-time gesture recognition by Nguyen which dealt with limb gestures, pattern matching was achieved on the sequence on a frameset by input into a statistical model that compared the reduced frameset data with recognizable gestures the motions by pattern recognition permits an operation based on the semantic meaning of the gesture to be performed by the computer.

Hit: A hit is the sending of a single file to a browser. The file type can be an HTML file, an image, an audio file, or other. Since a single web page request can have delivered with it a number of individual files, the number of hits from a site is a not an accurate indication of its actual number of visitors. It can be an indicator of traffic flow to the website but his is confused by proxy and cache servers that share frequently viewed files at a location on the Internet.

HTML: definition from the Whatis.com website at the URL http://whatis.com/WhatIs_Definition _Page/0,4152, 214031,00.html HTML (Hypertext Markup Language) is the set of "markup" symbols or codes inserted in a file intended for display on a World Wide Web browser. The markup tells the Web browser how to display a Web page's words and images for the user. The individual markup codes are referred to as elements (but people also refer to them as tags).

HTML is a standard recommended by the World Wide Web Consortium (W3C) <http://whatis.com/WhatIs_ Definition_Page/0,4152,213331,00.html>) and adhered to by the major browsers, Microsoft's Internet Explorer and Netscape's Navigator, which also provide some additional non-standard codes. The current version of HTML is HTML 4.0. However, both Internet Explorer and Netscape implement some features differently and provide non-standard extensions. Web developers using the more advanced features of HTML 4 may have to design pages for both browsers and send out the appropriate version to a user. Significant Internet Explorer 4.0 to current 5.5 and Netscape Navigator 4.0 and above have features in HTML 4 that are sometimes described in general as cascading sheets or dynamic HTML. What is sometimes referred to as HTML 5 is an extensible form of HTML called Extensible Hypertext Markup Language <See http://whatis.com/WhatIs_ Definition _Page/0,4152,213550,00.html>.

Impression: According to the "Basic Advertising Measures," from FAST, an ad industry group, an impression is "The count of a delivered basic advertising unit from an ad distribution point." Impressions are how most web advertising is sold and the cost is quoted in terms of the cost per thousand impressions (CPM).

Insertion order (IO): An insertion order is a formal, printed order to run an ad campaign. Typically, the insertion order identifies the campaign name, the web site receiving the order and the planner or buyer giving the order, the individual ads to be run (or who will provide them), the ad sizes, the campaign beginning and end dates, the CPM, the total cost, discounts to be applied, and reporting requirements and possible penalties or stipulations relative to the failure to deliver the impressions.

IP address: See <http://whatis.com/WhatIs_Definition _Page/0,4152,212381,00.html> for this definition which is based on Internet Protocol Version 4. In the most widely installed level of the Internet Protocol (IP) today, an IP address is a 32-binary digit number that identifies each sender or receiver of information that is sent in packet across the Internet. When you request an HTML page or send e-mail, the Internet Protocol part of TCP/IP includes your IP address in the message (in each of the packets) and sends it to the IP address that is obtained by looking up the domain name in the Uniform Resource Locator you requested or in the e-mail address you're sending a note to. At the other end, the recipient can see the IP address of the Web page requester or the e-mail sender and can respond by sending another message using the IP address it received.

An IP address has two parts: the identifier of a particular network on the Internet and an identifier of the particular device (which can be a server or a workstation) within that network. On the Internet itself—that is, between the router that move packets from one point to another along the route—only the network part of the address is looked at. The identity of the network and the device can be used to uniquely identify the session that is taking place without knowing exactly where the workstation and browser are located.

The Network Part of the IP Address

The Internet is really the interconnection of many individual networks (it's sometimes referred to as an internetwork). Therefore, the Internet Protocol (IP) is the set of rules for one network communicating with any other (or for broadcast messages, all other networks). Each network must know its own address on the Internet and that of any other networks with which it communicates. To be part of the Internet, an organization needs an Internet network number, which it can request from the Network Information Center (NIC). This unique network number is included in any packet sent out of the network onto the Internet.

The Local or Host Part of the IP Address

In addition to the network address or number, information is needed about which specific machine or host in a network is sending or receiving a message. Therefore, the IP address needs both the unique network number and a host number (which is unique within the network). (The host number is sometimes called a local or machine address.)

Part of the local address can identify a subnetwork or subnet address, which makes it easier for a network that is divided into several physical subnetworks (for examples, several different local area networks or) to handle many devices.

IP Address Classes and Their Formats

Since networks vary in size, there are four different address formats or classes to consider when applying to NIC for a network number:

Class A addresses are for large networks with many devices.

Class B addresses are for medium-sized networks.

Class C addresses are for small networks (fewer than 256 devices).

Class D addresses are multicast addresses.

The IP address is usually expressed as four decimal numbers, each representing eight bits, separated by periods. This is sometimes known as the dot address and, more technically, as dotted quad notation. For Class A IP addresses, the numbers would represent "network.local.local.local"; for a Class C IP address, they would represent "network.network.network.local". The number version of the IP address usually is represented by a name or series of names called the domain name.

Static vs. dynamic IP addresses is a very important detail in the IP world. The discussion above assumes that IP addresses are assigned on a static basis. In fact, many IP addresses are assigned dynamically from a pool. Many corporate networks and online services economize on the number of IP addresses they use by sharing a pool of IP addresses: among a large number of users. If you're an America Online user, for example, your IP address will vary from one logon session to the next because AOL is assigning it to you from a pool that is much smaller than AOL's 15 to 20 million subscribers. The dynamically assigned IP addresses are reused when another user/workstation is given a lease for the address by a DHCP (Dynamic Host Configuration Protocol) that lets network administrators manage centrally and automate the assignment of Internet Protocol (IP) addresses in an organization's network. To keep track of the users of the "leased" IP addresses a network router or firewall uses network address translation (NAT) to keep track of and translate inside (local area network) address and outside (Internet) addresses and sends the messages from the outside network to the station that has been assigned the IP address on the local area network (LAN) and vice versa.

Internet Protocol (IP): The Internet Protocol (IP) is the method or protocol by which data is sent from one computer to another on the Internet. IP provides the routing mechanism. Each computer (known as a host) on the Internet has at least one IP address that uniquely identifies it from all other computers on the Internet. When you send or receive data (for example, an e-mail note or a Web page), the message is divided into little chunks called packets. Each of these packets contains both the sender's Internet address and the receiver's address. Any packet is sent first to a gateway computer that understands a small part of the Internet. The gateway computer reads the destination address and forwards the packet to an adjacent gateway that in turn reads the destination address and so forth across the Internet until one gateway recognizes the packet as belonging to a computer within its immediate neighborhood or domain. That gateway then forwards the packet directly to the computer whose address is specified.

Because a message is divided into a number of packets, if necessary, each packet can be sent by a different route across the Internet. Packets can arrive in a different order than the order they were sent in. The Internet Protocol just delivers them. It's up to another protocol, the Transmission Control Protocol (TCP) to put them back in the right order.

IP is a connectionless protocol, which means that there is no established connection between the end points that are communicating. Each packet that travels through the Internet is treated as an independent unit of data without any relation to any other unit of data. (The reason the packets are put in the right order is TCP, the connection-oriented protocol that keeps track of the packet sequence in a message.)

See <http://www.edtn.com/encyclopedia/search?term=ip> and <http://whatis.com/WhatIs_Definition_Page/0,4152,214031,00.html>, the sources for this definition. The official definitions are in Internet Engineering Task Force's Request for Comments (RFC) 791. at <ftp://ftp.isi.edu/in-notes/rfc791.txt> and in IBM's Redbook, TCP/IP Tutorial and Technical Overview, in print and at <http://www.redbooks.ibm.com/abstracts/gg243376.html>.

(Ad) Inventory: Inventory is the total number of ad views or impressions that a web site has to sell over a given period of time (usually, inventory is figured by the month).

Knowledge Database: A knowledge database (composed from a collection of observed physical characteristics) are shown by example in U.S. Pat. No. 6,104,835 to Han entitled "Automatic knowledge database generation for classifying objects and systems therefor which discloses classifying objects according to a pre-defined set of primitives, or attributes, as an important tool in quantifying characteristics associated with a sample object taken from a population of similar objects. In this regard, object classification is useful where the parent population, is very large, for example, in categorizing and cataloging celestial images, or when the population is dynamic and its characteristics change over time, such as defects on semiconductor wafers, or magnetic disks, cataloging bacteria, and the like. Temporal or demographic shifts in object classes are identified by sampling objects, recording their attributes, and determining an object class appropriate to that object. In determining the object class of an object, a knowledge database ("KDB") typically compares the characteristics of an unknown object to the characteristics of pre-classified objects cataloged in the KDB. KDB's are generally encoded as machine-readable code in a computer system, and the comparison is performed by a computer to automatically classify the unknown object. Using the characteristic of known defects contained in the KDB that maps characteristics and location of known defects, a machine observes each sample defect under a video microscope and classifies each defect according to location and characteristic of 4 class (e.g., particle, pit, scratch, or contaminant).

Media broker: Media brokers aggregate sites and sell ad spaces on multiple sites for the convenience of advertisers and media planners and buyers.

Media buyer: A media buyer, at an advertising agency or large company, works with a media planner to allocate the money provided for an advertising campaign among specific print or online media (magazines, radio, TV, web sites and other media such as billboards, direct mail, email telemarketing etc.) The media buyer requests proposals and negotiates terms and final costs and places the advertising orders.

Network Address Translation: NAT is (Network Address Translation), an IETF standard that allows an organization to present itself to the Internet with one address. NAT converts the address of each LAN node into one IP address for the Internet and vice versa. It also serves as a firewall by keeping individual IP addresses hidden from the outside world the translation of an Internet Protocol address (IP address) used within one network to a different IP address known within another network. One network is designated the inside network and the other is the outside. Typically, a company maps its local inside network addresses to one or more global outside IP addresses and unmaps the global. IP addresses on incoming packets back into local IP addresses. This helps ensure security since each outgoing or incoming request must go through a translation process that also offers the opportunity to qualify or authenticate the request or match it to a previous request. NAT also conserves on the number of global IP addresses that a company needs and it lets the company use a single IP address in its communication with the world.

NAT is included as part of a router (See <http://www.edtn.com/encyclopedia/search?term=NAT>, <http://whatis.com/WhatIs_Definition_Page/0,4152,212924,00.html>) and often a corporate firewall. (See <http://whatis.com/WhatIs_Definition _Page/0,4152,212125,00.html>) Network administrators create a NAT table that does the global-to-local and local-to-global IP address mapping. NAT can also be used in conjunction with policy routing. NAT can be statically defined or it can be set up to dynamically translate from and to a pool of IP addresses.

Neural network: A modeling technique based on the observed behavior of biological neurons and used to mimic the performance of a system. It consists of a set of elements that start out connected in a random pattern, and, based upon operational feedback, are molded into the pattern required to generate the required results. A neural network is a system of circuits or programs and data structures that mimics the learning operations of the human brain and produces an "expert" output based on what it has learned in an supervised or unsupervised learning paradigm in which pairs of inputs and output patterns are presented to the network the sequences are recorded in a memory. A neural network is initially "trained" or fed large amounts of data and rules about data relationships. The An outer first layer of neurons receives input and learns to categorize inputs giving a weight to each input and outputting to a middle layer that combines multiple input layers and forwards the further abstracted information to an output layer. The output layer may then be feedback to correct the weights on the first or second layer to get optimal results. The FAQ at URL: <ftp://ftp.sas.com/pub/neural/FAQ.html> produced by saswss@unx.sas.com (Warren S. Sarle), Cary, N.C., USA is updated monthly. The basic feature of neural networks is the self-organizing or self-optimizing feature outlined in U.S. Pat. No. 4,325,259 to Cooper entitled "Self organizing general pattern class separator and identifier."

Well known to the users of this technology is the ability to score or scale the quality of the pattern matching for use in making decisions. Known uses for neural networks applications such as robotics, diagnosing, forecasting, image processing, especially handwritten character and symbol recognition and pattern recognition. Some patents are (1) in medical diagnostics for example Comanor's invention owned by Chiron disclosed in U.S. Pat. No. 5,860,917 entitled "Method and apparatus for predicting therapeutic outcomes" which uses SMILES similarity metric least squares for intelligent analysis of medical records. (2) In profiling persons in review of insurance claims and Federal income taxes others uses include for risk of fraud in credit card transactions, see Nestor.com Prism system and U.S. Pat. No. 5,822,741 to Fischthal at Lockheed Martin Corporation entitled "Neural Network/Conceptual Clustering Fraud Detection Architecture"; U.S. Pat. No. 5,819,226 to Gopinathan entitled "Fraud detection using predictive modeling"; U.S. Pat. No. 5,966,650 to Hobson entitled "Detecting mobile telephone misuse"; and U.S. Pat. No. 6,094,643 to Anderson et. al entitled "System for detecting counterfeit financial card fraud" in which counterfeit financial card fraud is detected based on the premise that the fraudulent activity will reflect itself in clustered groups of suspicious transactions. A system for detecting financial card fraud uses a computer database comprising financial card transaction data reported from a plurality of financial institutions. The transactions are scored by assigning weights to individual transactions to identify suspicious transactions. (3) in data mining, see U.S. Pat. No. 5,787,425 to Bigus entitled "Object-oriented data mining framework mechanism." (4) In character recognition, see U.S. Pat. No. 5,052,043 to Gaborski entitled "Neural network with back propagation controlled through an output confidence measure" is for OCR optical character recognition systems with attention to retraining the system only when characters change outside a predefined range, which through controlling back propagation and adjustment of neural weight and bias values through an output confidence measure, smoothly, rapidly and accurately adapts its response to actual changing input data (characters). Specifically, the results of appropriate actual unknown input characters, which have been recognized with an output confidence measure that lies within a pre-defined range, are used to adaptively re-train the network during pattern recognition. (5) in associative memories, also referred to as content addressable memories, which are widely used in the field of pattern matching and identification, expert systems and artificial intelligence see the widely used associative memory the Hopfield artificial neural network. Hopfield artificial neural networks are described in U.S. Pat. No. 4,660,166 to Hopfield entitled "Electronic Network for Collective Decision Based on Large Number of Connections Between Signals" by which means a decision may be made with only partial set of inputs.

Neural network knowledge: Neural network knowledge is acquired in layers. Neural networks are taught by successive presentation of sets of signals to their primary inputs with each signal set derived from a pattern belonging to a class of patterns, all having some common features or characteristics. Each time a set of signals is presented to the primary inputs, the synaptic weights must be adapted in order for the neural network to learn from this input. Basic knowledge is gained by training the neurons to differentiate and build up a memory of associations that may be called fuzzy logic. Neural network usually involves a large number of processors operating in parallel, each with its own small sphere of knowledge and access to data in its local memory. Networks that are more complex have deeper layers and feedforward systems use learned relationships stored in memory data to "feed forward" to higher layers of knowledge.

Opt-in e-mail: Opt-in e-mail is e-mail containing information or advertising that users explicitly request (opt) to receive. Typically, a web site invites its visitors to fill out forms identifying subject or product categories that interest them and about which they are willing to receive e-mail from anyone who might send it. The web site sells the names (with explicit or implicit permission from their visitors) to a company that specializes in collecting mailing lists that represent different interests. Whenever the mailing list company sells its lists to advertisers, the web site is paid a small amount for each name that it generated for the list. Opt-in e-mail usually starts with a statement that tells you that: you have previously agreed to receive such messages.

Pay-per-click: In pay-per-click advertising, the advertiser pays a certain amount for each clickthrough to the advertiser's web site. The amount paid per clickthrough is arranged at the time of the insertion order.

Pay-per-lead: In pay-per-lead advertising, the advertiser pays the source of for each sales lead generated, that is a finder's fee for every visitor that clicked on a site and then filled out a product interest form.

Pay-per-sale: Pay-per-sale is the customary way to pay web, sites that participate in affiliate programs, such as those of Amazon.com and Beyond.com where the source of the sale gets a fee for each sale.

Pay-per-view: Since this is the prevalent type of ad buying arrangement at larger web sites, this term tends to be used only when comparing this most prevalent method with pay-per-click and other methods.

Pixel: A pixel is a "picture element" a dot on the programmable color graphic file or in a computer image. The physical size of a pixel will approximate the physical size of the dot pitch (let's just call it the dot size) of the display. Sometimes a pixel will be larger than the physical size of the screen's dot (that is, a pixel will use more than one dot on the screen).

Proof of performance: Some advertisers want proof that the purchased ads have actually run and that clickthrough figures are accurate. There is no physical reprint or, tearsheets taken from a printed publication prove that an ad was run. On the web, there is no proof of performance standard. Media broker and the ad buyer usually check the web site to determine when the ads are actually running and require weekly figures during a campaign. Reports are used but some look directly at the figures, viewing the ad server or web site reporting tool via network management tools.

Psychographic characteristics: This is a term for personal interest information that is gathered by web sites by requesting it from users. For example, a web site could ask users to list the web sites that they visit most often. Advertisers could use this data to help create a demographic profile for that site.

Psychological/physiological profile: is a term unique to this invention.

Resolution: Resolution is the number of pixel (individual points of color) contained on a display monitor, expressed in terms of the number of pixels on the horizontal axis and the number on the vertical axis. The sharpness of the image on a display depends on the resolution and the size of the monitor. Larger monitors can show more detail because the size will be large enough to see the small displays. The 640×480 VGA (the old standard), 800×600 XGA (the new standard for a web page XGA-2 (1024×768 or 1280×1028 or more for large screens) are able to show a large amounts of information because the pixels are being spread over a larger number of inches at a reasonable size. A 15-inch monitor at 1024×768 resolution would be displaying a small banner in a very tiny area and would require a very high number of dots per inch to show the details. The PDA (Portable Digital Assistant Palm Pilot device or Pocket PC) has a smaller resolution of A mobile phone display is only capable of Rich media: Rich media is advertising that contains perceptual or interactive elements more elaborate than the usual banner ad. Today, the term is often used for banner ads with popup menus that let the visitor select a particular page to link to on the advertiser's site. Rich media ads are generally more challenging to create and to serve. Some early studies have shown that rich media ads tend to be more effective than ordinary animated banner ads.

ROI, Return on Investment: is measure of how successful an ad or campaign was in terms of what sales revenues were returned for the money invested.

Splash page: A splash page (also known as an interstitial) is a preliminary page that runs before the regular home page of a web site and usually promotes a particular site feature or provides advertising. A splash page is often new browser window that contains a rich media video or animation that jumps to the home page after a short period of time.

Sponsor: A Sponsor is an advertiser who has sponsored an ad and has also helped sponsor or sustain the web site itself. It can also mean an advertiser that has a special relationship with the web site and supports a special feature of a web site.

Targeting: Targeting is purchasing ad space on web sites that match audience and campaign objective requirements.

Transmission Control Protocol: TCP (Transmission Control Protocol) is a method or protocol used along with the Internet Protocol (I P) to send data in the form of message units between computers over the Internet. While IP takes care of handling the actual delivery of the data, TCP takes care of keeping track of the individual units of data (called packet) that a message is divided into for efficient routing through the Internet. TCP is known as a connection-oriented protocol, which means that TCP provides transport functions, which ensures that the total amount of bytes sent is received correctly at the other end. UDP is an alternate transport that does not guarantee delivery. UDP is widely used for real-time voice and video transmissions where erroneous packets are not retransmitted. TCP is responsible for ensuring that a message is divided into the packets that IP manages and is responsible for reassembling the packets back into the complete message at the other end.

Internet Engineering Task Force (IETF) Request for Comments 793. DARPA 1981 Internet standards known a RFC. <http://cnswww.cns.cwru.edu/net/odds-ends/rfc/rfc793>

Unique visitor: A unique visitor is someone with a unique address who is entering a web site for the first time that day (or some other specified period). Thus, a visitor that returns within the same day is not counted twice. A unique visitors count lets ad people know how many different people there are in the audience during the time period, but not how much they used the site during the period.

Unique visit: A unique visit is a count for someone who is entering a web site from another sited for the first time on a single day or later time even on that day or some within some other specified period. Thus, a visitor that returns to the site can be counted for each visit from outside the site, for example in response to banner ads leaving the web site and returning later.

User session: A user session is someone with a unique address that enters or reenters a web site each day (or some other specified period). A user session is can be determined by counting only those users that haven't reentered the site within the past 20 minutes or a similar period. User sessions indicate total site activity better than "unique visitors" since they indicate frequency of use and can be used to count repeat visits.

View: A view is either an ad view or a page view. Usually an ad view is what's meant. There can be multiple ad views per page views. View counting should consider that a small percentage of users choose to turn the graphics off (not display the images) in their browser.

Visit: A visit is a web user with a unique address entering a web site at some page for the first time that day (or for the first time in a lesser time period). The number of visits is roughly equivalent to the number of different people that visit a site. This term is ambiguous unless the user defines it, since it could mean a user session or it could mean a unique visitor that day.

DESCRIPTION OF THE PRIOR ART

The World Wide Web is more than an information Superhighway, a source of information. WWW has become an attractive multimedia shopping mall. The more time a happy consumer spends at the merchandiser, the more chances to sell products to the visitor. The present invention has objectives that are distinguishable from presently used web media selection systems and web content controls that are intended to satisfy customer viewer's expressed likes and dislikes and by paying constant attention to the selection of media programming that the viewer has chosen. According to Wexler probably the most common form of social navigation is information recommendation, sometimes referred to as social filtering [fn20 Shardanand, Upendra & Pattie Maes. "Social Information Filtering: Algorithms for Automating 'Word of Mouth'," Proceedings of CHI'95 Conference on Human Factors in Computing Systems, ACM Press, 1995.]. Information, usually in the form of ratings, from other users is applied to help the current user. This is done either by selecting one or a few items from a large database of potentially recommendable items, or by ordering, rating or filtering information items based on past ratings data. Systems which fall into this category include the Bellcore video recommender [fn7 Hill, Stead, Rosenstein & Furnas. "Recommending and Evaluating Choices in a Virtual Community of Use," Proceedings of CHI'95 Conference on Human Factors in Computing Systems, ACM Press, 1995.], the MIT Media Lab's HOMR music-recommendation system [fn19 Salton, Gerard. The SMART System: Experiments in Automatic Document Processing, Prentice Hall, 1971.], the Do-I-Care Agent (DICA) for Web pages [fn21 Starr, Ackerman & Pazzani. "Do-I-Care: A Collaborative Web Agent," Proceedings of CHI'96 Conference on Human Factors in Computing Systems, ACM Press, 1996.], and the Usenet news rating system GroupLens [16 Miller, Riedl, & Konstan. "Experiences with GroupLens: Making Usenet useful again," Proceedings of the 1997

Usenix Winter Technical Conference, January 1997.]. Hill and Terveen's PHOAKS (People Helping One Another Know Stuff) system [fn9 Hill, Will & Loren Terveen. "Using Frequency-of-Mention in Public Conversations for Social Filtering," *Proceedings of CSCW'96 Conference on Computer-Supported Cooperative Work*, ACM Press, 1996] uses FAQs and other postings to select URLs for recommendation.

The invention does something entirely different. BioNet method and system allows monitoring of physiologic and psychological signals that indicate stress, emotion, moods or boredom in the context before a sale and help the web content provider maintain the interests and buying momentum of a viewer.

The use of viewer surveys and monitoring of browser activity to controls selection of media presented on a website and used to control selection of ads presented to viewers based on a profile of viewer interests is well known to the website proprietors based that rely upon individually collected interest surveys and large scale demographic studies for generating increased activity that leads to sales. With multiple ad views on several banners and sidebars, it is difficult to attribute behavior to a particular ad view. At a given moment monitoring viewer attention and the immediate viewer response in real time in sync with the views can give advertisers a better measure of viewer response. Recently the multitude of portal websites open with a membership questionnaire and offer incentives such as customized newsletters, product finders, price watchers, daily reminders, free electronic mailboxes, customized web pages, personalized product catalogs and affinity programs such as discount coupons frequent viewer miles, contests, prizes raffles and giveaways to get people to come back again and again. More specifically, advertising controls used to select media for websites heretofore devised and utilized survey tools that are known to consist basically of familiar expected questionnaires on preferred choices in books music movies and other products coupled with background demographic information and "collaborative filtering or Group Lens" software for comparing surveys and collecting demographics that intend to suggest what the viewer is most likely to want based on what similar viewers have like. The statistics help the advertiser reach a targeted audience and make the selection of the ever preset "banner ad" that is placed on the top of many web pages. Ad panning systems are moving toward a real time analysis of consumer groups to ads. The real-time speed of analysis permits customization or personalization of ads to fit the group of consumers or the individual. The ad cost per lead or cost per click may be verified and rates for ads may be set based on the targeted audience and the responsiveness of the audience. Vendors make competitive claims about how effective the systems are at prediction consumer responses to future ad campaign.

Personality profile information may be useful in making guided sales because the response is different for different types of persons. Online training question and answers offers opportunity to collect profile information while a person performs online training. Answering the question as part of an online negotiation-training program can give personal insights. For example answering the Question: Choose the three most common fears you will encounter when you are negotiating? Failure, Humiliation, Suffering, Loss, The unknown. These fears need to be dealt with in the sales process. Information on how the viewer responds can be obtained explicitly by surveyor implicitly by observation of behavior within contest. The most widely known fear used in sales is the limited time promotion that works on the fear of losing a good deal. "Act now the price will never be better!" The questionnaire is not necessary since valuable personal information can be inferred by observing behaviors and keeping a record of sales after presentations that work on the limited time offer principle. The fear of loss can be ascertained by the behavior that shows the consumer taking the bait and buying.

FIG. 2 shows alternative models that APT Applied Predictive Technology claims to use multiple algorithms to identify the optimal analytical method to solve each predictive challenge. In comparison, APT says competing approaches rely upon one and only one predictive statistical technique, exposing users to its flaws when it is not the best predictor of future results. APT builds competing models and employs genetic algorithms to choose the best approach. Modeling techniques employed include: neural networks, collaborative filtering (clustering/filtering), logistic regression decision trees, and linear regression. Neural networks appear to be the best method.

Significant advertising revenues are being generated by the click through ads in which the browser viewer follows an ad link to another page and proceeds through to a sale. Web site providers that displayed the ad that the viewer selected and clicked-on and that eventually led to a sale may receive pennies or larger amounts for each viewer who traversed the link and visited an advertisers web page. Notwithstanding the designs encompassed by the crowded prior art which have been developed for the fulfillment of consumer objectives and meeting activity monitoring requirements of ad agencies and web site content management, which makes the selections of web pages, pictures, music and spoken audio, animation, streaming video and other presentations BioNet method and system offers a minimally invasive means to get immediate confirmation of the desires and dislikes of the browser viewer at several steps before the actual sale and permits the website content managers to develop a database which contains the history of the steps taken before the sale that is much more than a click-through recording. The database includes a physiological, psychological and emotional sequence before the sale occurs.

The BioNet method and system is suitable for use with any website that is able to categorize web displays according to at least three: phases of a purchase and identify the best media responses to emotional sales barriers when indicated by electronically monitored physiological and psychological signals are transmitted to a "ppd" physiologic/psychological database server and may be a part integral to website or an add-on service reached through the internet. The categorization of purchase to a limited number of phases which outline the general track of events that occur in the time preceding a sale makes the planning of media easier by reducing the decision or choices and reduces the computational demands of the pattern recognition of a time series of events by making "training solution" assumptions that apply to neural networks and database clusters called emotional footprints by the inventors. Nonetheless, the variety of psychological and physiological input variables allows customization of a system to meet individual situations based on the Escores for various personality attributes, which are identifiable by legacy (already stored) individual profiles, current Behavioral/Emotional-Attention Indicators responses or candidate profiles associated with the specific product being sold or.

As is often desired during an ad campaign, website ad sponsors have scheduled for standard web content presentation and that standard material can override media recommendations if desired. When the conditions for override operation are met, the website controls of the present invention will allow standard web content to be displayed. When override is not present particularly when the final pre sale phases: are reached recommend media content with a theme that based on recommendations of the ppd server assists the website selection of the web page media content and theme based on recommendation coming from the ppd server, that use historically confirmed psychological/psychological indicators.

Some web site media content controllers maintain an internal database. The Macromedia Real Time Like Minds™ system is an example of one such all-inclusive system. As is seen in FIG. 5 ?????? Frequently websites use a distributed system in which the three tiered system Storage in back end database, mid level business logic and Desktop browser client level display. Extended HTML or XML is used for management of the distributed systems. Macromedia Enterprise LikeMinds™ is an example of the distributed system.

Guided selling is a new type of interactive sales system that goes one step further to refine the computer interaction to a level that approaches the actions of a virtual sales assistant that interacts in a human conversational fashion with the web viewers. U.S. Pat. No. 6,070,149 to Tavor, et al discloses Virtual sales personnel that enables users over a network or over the WWW to interact with an interactive sales representative system for providing sales guidance. The system offers the user products, services, or ideas (the "products") according to parameters collected from the user. The system guides the customer to retrieve the desired products. If the system does not have a product matched to the customer requirements, preferably it will operate a mechanism for suggesting alternatives that are the closest to the customer requirements and for suggesting alternatives that have the greater likelihood of leading to a decision to buy or select. SAS mentions the guided selling technology as applied to customer websites and cites the need for fewer live sales support personnel.

The pattern recognizer is preferably a neural network which has gained much complexity and ability to discriminate in evolution from U.S. Pat. No. 5,355,436 to Shin and Sridhar describes a "Single layer neural network system for performing separable and non linearly separable logical operations using complex weights." Shin used a single neuron network, which may be configured in a single layer is known as a perceptron known by the MP acronym for McCulloch Pitts model of brain interconnected neurons. In general, a perceptron accepts multiple inputs, multiplies each by a weight, sums the weighted inputs, subtracts a threshold, and limits the resulting signal, such as by passing it through a hard limiting nonlinearity. A perceptron is described in W. McCulloch and W. Pitts, "A Logical Calculus of the Ideas Immanent in Nervous Activity", Bulletin of Mathematical Biophysics, Vol. 5, pp. 115–133, 1943. Further development beyond to a difference type or non-MP neuron cells was disclosed in U.S. Pat. No. 5,359,700 to Seligson of Intel entitled "Neural network incorporating difference neurons." An artificial neural network incorporating difference type, non-MP (McCullough-Pitts) neuron cells and a method and apparatus for training this network. And finally, Cooper et al in U.S. Pat. No. 5,054,094 discloses a parallel multi unit adaptive nonlinear class separator and identifier. It is described as a system for separating and identifying classes of patterns or events which are not necessarily linearly separable. During a training process of the system, new prototypes are created when prior stored prototypes fail to properly classify an input pattern, and previously stored prototypes are modified when an input pattern falls within the sphere of influence of a prototype associated with a different class than the input pattern. The particular neural network that is used is not important. Of critical importance is the ability of the system to learn and be self correcting. The physiologic Biosignals heart rate, blood pressure skin resistance and skin temperature as well as gestures as mood indicators are critical nonverbal signals which have no immediate action but rather upon recognition of a pattern of subsequent actions may be used as a predictive indicator for future behavior. Analysis of past behaviors and accompanying Biosignal and gesture recognition events makes the BioNet system respond more quickly than inference based systems that must wait for a clickthrough type event to begin to learn.

The present invention operates or may operate independently from other website content monitoring and control systems seen in the prior art. Alternatively, it may be embedded into a real-time system that does not require a distributed set of servers for logic and database storage functions.

One media content controlling method being electronic monitoring of browser activity sensing of content viewed and duration of display and buyer behavior, transitions to next viewed media pages transmitting viewer information to a central database, comparing the viewer data with other similar viewers and deriving a suggested media presentations based upon interests expressed by other viewers that have similar characteristics. This is the so called collaborative filtering also described in NetConnections patent and Miller's Group lens technology.

Electronic transmission of media is driven from a website or content controlled ad servers that are linked to multiple websites by small "one-pixel" files in web pages that send a web page with an embedded "web bug" that makes a call out to the ad server to send the information to the browsers.

Present computer systems include display input devices network connections and do not have physiologic input sensors that transmit the BioData to the workstation or computer which forwards pertinent information to the network.

When a viewer is on a website monitoring browser activity especially the successful click through activity that leads to sales includes recording numbers of views of a particular page, time spent on the page, progression to other pages on the site and eventually sales are critical to the operation of the database and selection of media by the recommendation system.

A first standard browser communication filtering method for recommending being such that the source of the click is tracked to determine the referral site from which the user browser originated the click and arrived at the ad website. This is the transversal or web link filtering method collects clickthrough information, compares successful sales with the source of the buyers, and in affiliate programs pays referring sites that result in sales.

A second browser communication filtering method being such that filtering and clustering is used improved upon to minimize the effort needed to make the group analysis. The so called filtering and clustering method is known as collaborative filtering when multiple users and websites are used to collect information about purchases and requests so that a demographic group of consumers independent of.

A third browser communication filtering method being such a neural network is employed in a context of a first ad viewing to learn to the characterize the behavior of an individual consumer and establish membership of the individual in groups of like consumers and in a second context of later viewing to use the characterization to select media content and thematic approach for later views by the same consumer and group members and to characterize the behavior of that individual and group members at second context views and in other contexts.

Newer web site management tools and media control systems use. A possible fourth method in this invention both the first and second methods are combined in one filter. This is functional where only one web server is intended to use the correlated data for user preferences and choice of preferred media. Preferred theme and media choice is from the vendor and consumer is the theme and choice that leads most consistently to a sale of goods or acquisition of information or services.

A fifth method of modification of a website content manager employs a decision tree or logistic model for selection of media based on statistic like and dislikes based on average Bayesian.

The preferred embodiment for the system is a self correcting learning system one of several multilayer a neural network implementations which learn individual preferences/recommendations and group preferences/recommendations are employed. A hierarchy of choices for recommendations based on individuals, groups and media providers. What is unique to the system is the ability of the web content provider to override the recommendations and use a "campaign approach" or force the use of standard media and theme choices and force the selection of ads shown to viewers to evaluate specific new materials. This override permits testing of media on viewers and collection of data for diverse individuals and groups of individual where new media has been developed. This also can be used for forced repetition saturation campaigns. Biosignal responses, click through and buying responses are observed and the system learns and evaluates the responses even before the clickthrough has been completed.

FIG. 13 shows the hierarchy of choices for recommendation that requires a threshold for both individual and group recommendations. An individual measure of confidence in the individual recommendation based on individual preferences is desired to be above an individual confidence threshold. If the individual measure confidence is not sufficient to trust the recommendation, the website content provider may use the group data to determine a group recommendation instead of the individual recommendation. A group measure of confidence in the group recommendations based on group preferences is desired to be above a group confidence threshold. If the group measure of recommendation is not sufficient to trust the group recommendation or if the default is required by the advertiser the default content and theme will be used.

Principle of the Invention

Internet browsers are viewed by consumers and are considered an excellent medium for ads and making "on-line" sales. The problem that consumer viewers often browse and select products but abandon the online shopping cart before a sale is completed.

The inventors' experience that more customers achieve a satisfactory result is a closed sale for the salesperson in a situation where a live salesperson is able to answer customer questions and understand and respond to the unspoken objections shown by the customers body language, gestures, eye contact and tone of voice that are reliable indicators if the potential buyer has problems with the sale. BioNet method, system and personalized web content manager is responsive to browser viewers' psychological preferences, behavioral responses and physiologic stress indicators that are available through the use of psychological/physiological monitoring devices attached to the browser equipment, thus preserving website's efficient operation. Preservation of buying momentum and continued browsing with minimal delays are primary concerns addressed by the invention.

While these devices fulfill their respective, particular objectives and requirements, the aforementioned patents do not disclose a new BioNet method, system and personalized web content manager that immediately responds to real time indications of stress or interest of the website viewer. The inventive device includes Biosignal sensors, hardware for obtaining physiologic information, and gesture recognition, means for computer analysis of the Biosignals, including taking a baseline measure before media is presented and recording perturbations from baseline, means for sending the information from a client web browser to a computer network that keeps a history of viewer interactions with the website including those actions which preceded earlier sales for purposes of creating a knowledgebase of predictable consumer behaviors.

In these respects, the BioNet method, system and personalized web content manager responsive to browser viewers' psychological preferences, behavioral responses and physiologic stress indicators according to the present invention substantially departs from the conventional concepts and designs of the prior art, and in so doing provides a method and apparatus primarily developed for receiving immediate consumer feedback for the purpose of selectively advising websites on what media will meet the content and themes desired by the consumer. Immediate feedback is obtained by using the stress or discomfort indicated through Biosignals made available by selected Biosignal sensors and combined with database information that includes the context of the viewing situation, the psychological profile of the viewer, and particularly includes the recognizable pathway that includes steps at least the last three steps before a sale is recorded. Based upon the context and viewer history website content provider is given suggestions for presentations that satisfy viewers and achieve maximum sales efficiency, that will lead to quicker sales and fewer abandoned visits.

SUMMARY OF THE INVENTION

In view of the foregoing disadvantages inherent in the known types of website media content and theme controls used to provide a content to a web viewer the present browser viewer's physiologic/psychological information to a website content provider so that the information can be transmitted to browser viewers now present in the prior art, the present invention provides a new BioNet method, system and personalized web content manager responsive to browser viewers' psychological preferences, behavioral responses and physiologic stress indicators construction wherein the same can be utilized for selectively presenting media choices to the consumer with aims to reach a maximum satisfaction of viewer desires without a loss of momentum toward a with sale with minimum time consumption by the user and minimum bandwidth consumption by the media selected.

The general purpose of the present invention, which will be described subsequently in greater detail, is to provide a new BioNet method, system and personalized web content manager responsive to browser viewers' psychological preferences, behavioral responses and physiologic stress indicators apparatus and method which has many of the advantages of the present personalized web content managers and includes many novel features that result in a new BioNet method, system and personalized web content manager responsive to browser viewers' psychological preferences, behavioral responses and physiologic stress indicators which is not anticipated, rendered obvious, suggested, or even implied by any of the prior art portals website controls, website ad monitoring systems controls used to control and suggest media content supplied to a browser viewer, either alone or in any combination thereof.

To attain this, the present invention generally comprises a web browser connected to a network, browser being software running on a digital computer input output devices capable of text display, optionally sound and multimedia display, and including the standard button keyboard or mouse, specialized physiological input accessories acquire signals; further comprising a database for storing user preferences, psychological data and physiological data, an analysis component for identifying patterns of activities for individuals and groups of individuals using the browser, and a recommending component for recommending to a web content provider the media type and message themes to be viewed by the browser user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. In addition, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and software practitioners in the art who are not familiar with patent or legal terms or phraseology, to determine quickly from a cursory inspection the essence of the technical disclosure of the application. The abstract is neither intended to restrictively define the invention of the application, which is measured by the claims, nor is the abstract intended to limit the scope of the invention in any way.

It is therefore an object of the present invention to provide a new BioNet method, system and personalized web content manager responsive to browser viewers' psychological preferences, behavioral responses and physiologic stress indicators which is not anticipated, rendered obvious, suggested, or even implied by any of the prior art website content controls used to control web pages, rich multimedia and ads to a consumer web browser, either alone or in any combination thereof for viewing on any of new wireless media browsers including PDA's (personal digital assistants PALM OS or Pocket PC), cell phones, pagers that are soon to be available with Bluetooth, G3, and the WAP Wireless Application Protocol.

It is another object of the present invention to provide a new BioNet method, system and personalized web content manager responsive to browser viewers' psychological preferences, behavioral responses and physiologic stress indicators which may be easily and efficiently manufactured and marketed.

It is a further object of the present invention to provide a new BioNet method, system and personalized web content manager responsive to browser viewers' psychological preferences, behavioral responses and physiologic stress indicators which is of a flexible and reliable architecture scalable for use on systems with web browsers on various personal computers and internet appliances that use operating Microsoft Windows, Linux, OS/2, PALM OS, Windows CE severed by web servers that operate on a variety of UNIX, Windows NT, IBM AIX, Sun Solaris, Apple Macintosh OS n-X others on various server platforms.

An even further object of the present invention is to provide a new personalized web content manager responsive to browser viewers' psychological preferences, behavioral responses and physiologic stress indicators which is susceptible of a low cost of programming and distribution with regard to both media and labor, and which accordingly is then susceptible of low prices of sale to the advertisers and media providers, thereby making such personalized web content manager responsive to browser viewers' psychological preferences, behavioral responses and physiologic stress indicators economically available to the buying public.

Still another object of the present invention is to provide a new BioNet method, system and personal web content manager responsive to behavioral responses and physiologic stress indicators which provides in the apparatuses and methods of the prior art some of the advantages thereof, while simultaneously overcoming some of the delayed response of existing recommendation systems that must wait for explicit action via user click or input before deciding on further recommendations and disadvantages normally associated therewith.

Still another object of the present invention is to provide a new BioNet method, system and personalized web content manager responsive to browser viewers' psychological preferences, behavioral responses and physiologic stress indicators for selectively recommending to the web content provider the theme to be pursued on the website ad media presentations based on signal received telling the consumer responses to ads before behavioral actions indicate the consumer's choice.

Still yet another object of the present invention is to provide a new BioNet method, system and personalized web content manager responsive to browser viewers' psychological preferences, behavioral responses and physiologic stress indicators that is self correcting, in response to changes of individual responses. Where suggested media content and themes do not match the desired result showing a greater inclination toward a sale according to legacy history rules proposed for an individual, the system can fall back from individual profile matching to group profile matching or to default campaign or product profile matching.

Even still another object of the present invention is to provide a new BioNet method, system and personalized web content manager responsive to browser viewers' psychological preferences, behavioral responses and physiologic stress indicators is useable as an add on module to existing web site media selection controls.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference, should be had to the accompanying drawings and descriptive matter in which there is illustrated preferred embodiments of the invention.

BRIEF DESCRIPTION OF THE DRAWINGS

The invention, as well as the following detailed description of preferred embodiments, will be better understood and objects other than those set forth above will become apparent when consideration is given to the following detailed description thereof. Such description makes reference to the annexed drawings that are included by way of example, and not by way of limitation with regard to the claimed invention.

FIG. 1 generally illustrates the cycle of operation of the present invention.

FIG. 2 is a PRIOR ART evaluation chart by APT Applied Predictive Technology Chart that shows a comparison of effectiveness of various models used to predict content that applies to an apparel website. <http://www.predictivetechnologies.com/images/right_tool.gif>

FIG. 3 is a PRIOR ART illustration FIG. 3 of a client server exchange session involving the access control and monitoring method of the Levergood U.S. Pat. No. 5,708,780.

FIG. 3A is an illustration of a client server exchange session involving the access control and monitoring method using a session identifier psychological physiological indicator transmitted over the network.

FIG. 3B is an example of an apparel website using Microsoft Active Server Page implementation of the web server and browser viewer that uses database elements

FIG. 4 is a diagram of Alkons' Dynamically-Stable Associative Learning Neural Network System which also may be used in BioNet System and personalized web content managers FIG. 4A is a PRIOR ART multilevel neural network block diagram of the neural network in U.S. Pat. No. 5,054,093 Cooper A Parallel, multiunit, adaptive, nonlinear pattern class separator and identifier.

FIG. 5 is a schematic block diagram of the BioNet System and personalized web content manager responsive to browser viewers' psychological preferences, behavioral responses and physiological stress indicators of the present invention with a three tier setup.

FIG. 8 is an example consumer database that is a flat representation of multidimensional databases where each column in an OLAP online analytical processing database joins several databases A demographic, B general, C biosignals, D Medical, E credit score, F psychocognitive (survey), G Buying history (BuyScore), H cookie data and I behavioral emotional states.

FIG. 9 is a modified a schematic diagram of the network dataflow to and from Web server 52, Client and Database and Financial Credit Debit server of the present invention using an website interposed between the BDS Buy Data ppd database (Physiologic/Psychological Server databases where BuyScore E-Score and kept and suggestions are sent Web server.

FIG. 10 is a scenario of a web site visit illustrated by a pathway diagram of page views prompts and activities as two different visitors John and Joe traverse web site pages, which are selected based on personal preferences and responses of the consumers.

FIG. 14 is A Biomouse Process Chart.

FIG. 15 is FIGS. 1+2 from U.S. patent application Ser. No. 09/497,096.

DESCRIPTION OF THE PREFERRED EMBODIMENT

Figure 3C:
FIG. 3C is an online slide viewer presentation by SAS that outlines the advantages of Managing Customer Relationships is the key to Win—Win E-commerce.

With reference now to the drawings, and in particular to FIGS. 1 through 13 thereof, a new BioNet System and personalized web content manager responsive to browser viewers' psychological preferences, behavioral responses and physiological stress indicators embodying the principles and concepts of the present invention and generally designated by the reference numeral 10 will be described.

Figure 3D:
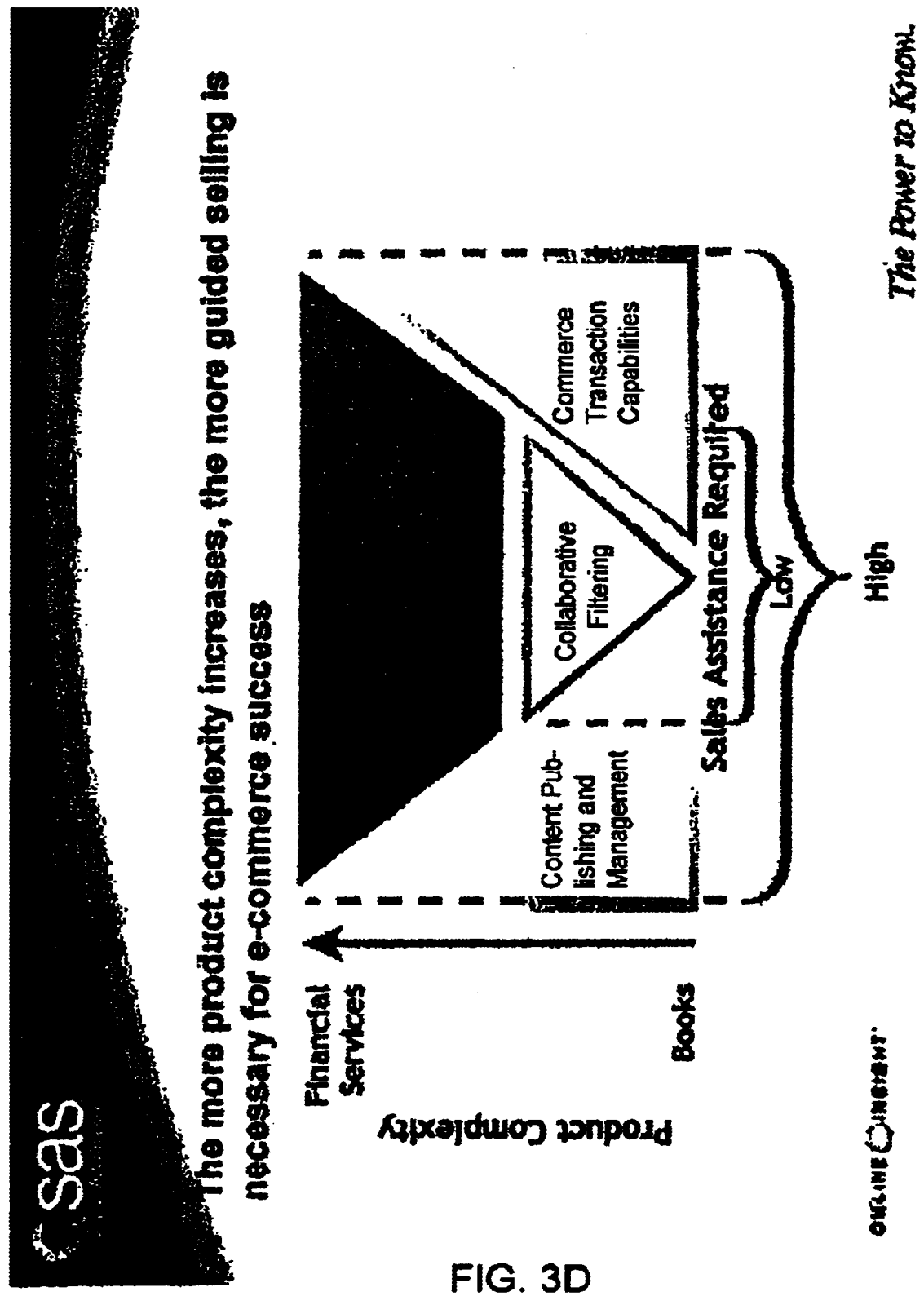
FIG. 3D is another slide viewer presentation by SAS that illustrates the advantages of guided selling for more complex sales that could otherwise require sales staff actions to support the viewer customer.

More specifically, it will be noted that the workstation in FIG. 3 of U.S. Pat. No. 5,784,608 herein incorporated as FIG. 7 included in drawings is a computer system, such as a workstation, personal computer or other processing apparatus in which the client 50 operates a browser 200 or a server 150 may be operative is illustrated in FIG. 8 with a browser, various biosensors and a voice stress analyzer. In a similar manner a web appliance browser, two way email device, minibrowser devices using WAP, wireless application protocol, new 3G wireless standard, or NTT DoCoMo Japanese standard may be a platform for a browser and biosensors and perhaps a voice stress analyzer. A workstation in which one implementation of the present invention may be practiced includes system 300, which comprises a bus or other communication means 301 for communicating information, and a processing means 302 coupled with bus 301 for processing information. System 300 further comprises a random access memory (RAM) or other volatile storage device 304 (referred to as main memory), coupled to bus 301 for storing information and instructions to be executed by processor 302. Arrows such as 67 represent the system bus architecture of computer system 1. However, the bus is illustrative of any interconnection scheme serving to link the subsystems. For example, a local bus could be utilized to connect the central processor to the system memory and the display adapter. A wireless interconnection scheme could link processor display adapter and memory. Main memory 304 also may be used for storing temporary variables or other intermediate information during execution of instructions by processor 302. System 300 also comprises a read only memory (ROM) and/or other static storage device 306 coupled to bus 301 for storing static information and instructions for processor 302, and a data storage device 307 such as a magnetic disk or optical disk and its corresponding disk drive both fixed and removable. Data storage device 307 is coupled to bus 301 for storing information and instructions. This may be used for storage of the various files to be described here including profiles, indices, temporary cached web information, topics, and files.

System 300 may further be coupled to a display device 321, such as a cathode ray tube (CRT) or liquid crystal display (LCD) or a visor, which is coupled to bus 301, for displaying information to a computer user. Such a display 321 may further be coupled to bus 301 via a frame buffer 310, which information such as a single or multiple frames or images for display upon display device 321. An alphanumeric input device 331, including alphanumeric and other keys, may also be coupled to bus 301 for communicating information and command selections to processor 302. An additional user input device is cursor control 332, such as a mouse, a push-pointer, a trackball, stylus, or cursor direction keys, coupled to bus 301 for communicating direction information and command selections to processor 302, and for controlling cursor movement on display 321.

Note, also, that any or all of the components of system 300 and associated hardware may be used in various embodiments, however, it can be appreciated that any configuration of the system may be used for various purposes according to the particular implementation. Bio Remote control 340, BioPhone wireless 341, and 2way BioPager 342 and BioPalm Pocket PC are self contained wireless devices include within a system on a chip or miniature system with the RAM ROM CPU and Mass storage as well as BioData sensors and device controls and minibrowser displays and sometimes audio speakers or headphones.

In one embodiment, system 300 is one of the Sun Microsystems® brand family of workstations such as the SPARC-station brand workstation manufactured by Sun Microsystems® of Mountain View, Calif. Processor 302 may be one of the SPARC brand microprocessors manufactured by Sun Microsystems®, Inc. of Mountain View, Calif. Note that the following discussion of various embodiments discussed herein will refer specifically to a series of routines which are generated in a high-level programming language (e.g., the PERL, JAVA, PYTHON, SMALLTALK interpretive and scripting languages) which is interpreted and/or executed in system 300 at run-time. These further are used in conjunction with the browser and server software available from NCSA, MOSAIC NETACAPE MICROSOFT and other SPYGLASS licenses including the specification of the appearance of displays in HTML. One skilled in the art appreciates that the following methods and apparatus may be implemented in special purpose hardware devices, such as discrete logic devices, large scale integrated circuits (LSI's), application-specific integrated circuits (ASIC's), or other specialized hardware. Other programming languages, C, BasicC, C++ and other Operating systems such as Unix, Posix, and variations of Linux platforms may be utilized.

Another embodiment Web Server platform comprises an IBM RISC System/6000 computer running the AIX (Advanced Interactive Executive) Operating System and a Web server program, such as Netscape Enterprise Server Version 2.0, that supports interface extensions. The platform also includes a graphical user interface (GUI) for management and administration. The various models of the RISC-based computers are described in many publications of the IBM Corporation, for example, RISC System 6000, 7013 and 7016 POWERstation and POWERserver While the above platform is useful, any other suitable hardware/operating system/Web server combinations may be used. Accordingly, the web server description here has equal application to apparatus having similar components and functions.

Biosignal processing could occur at a central location if signals could be transmitted and received reliably at a central computer. One problem for delivery of Biosignals is the availability of Broadband service to consumers homes. Cable modems and DSL are expected to become more popular in coming years. More bandwidth in the last mile to the consumer's home would permit centralized monitoring of Biosignals that are transmitted in packets to a central server instead of being analyzed at the browser system. August, 2000 "Emarketer" reported second quarter growth in US DSL was at 59%, according to TeleChoice. The number of lines in service jumped 754,770 to 1.2 million and predicted there were likely to be 10 million DSL and cable TV connections in the US in the next three or four years.

Figure 4B:
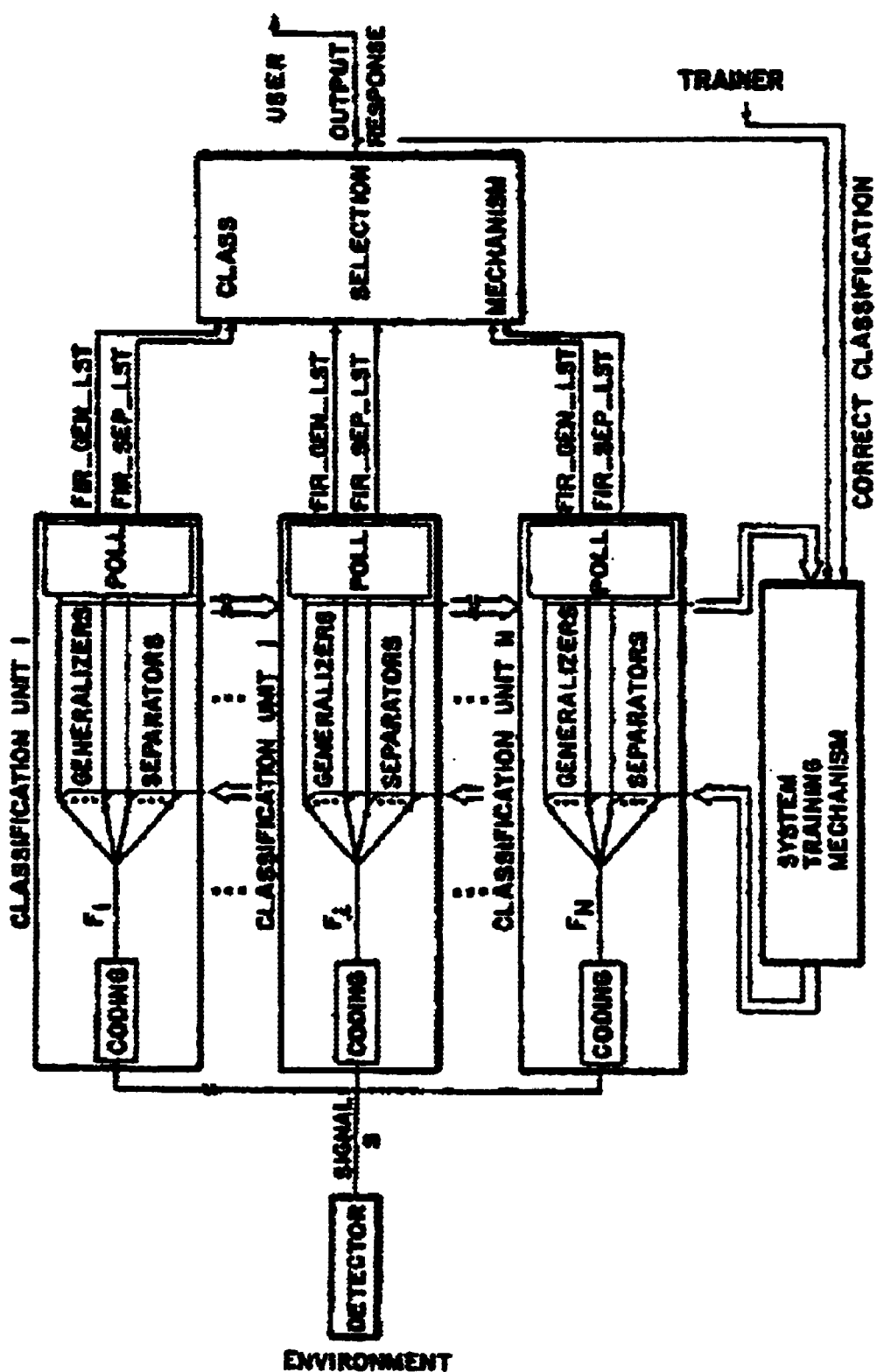
FIG. 4B is a PRIOR ART multilevel neural network block diagram of the Nestor Multilevel Neural Network in U.S. Pat. No. 4,958,093 to O'Reilly.
Figure 6:
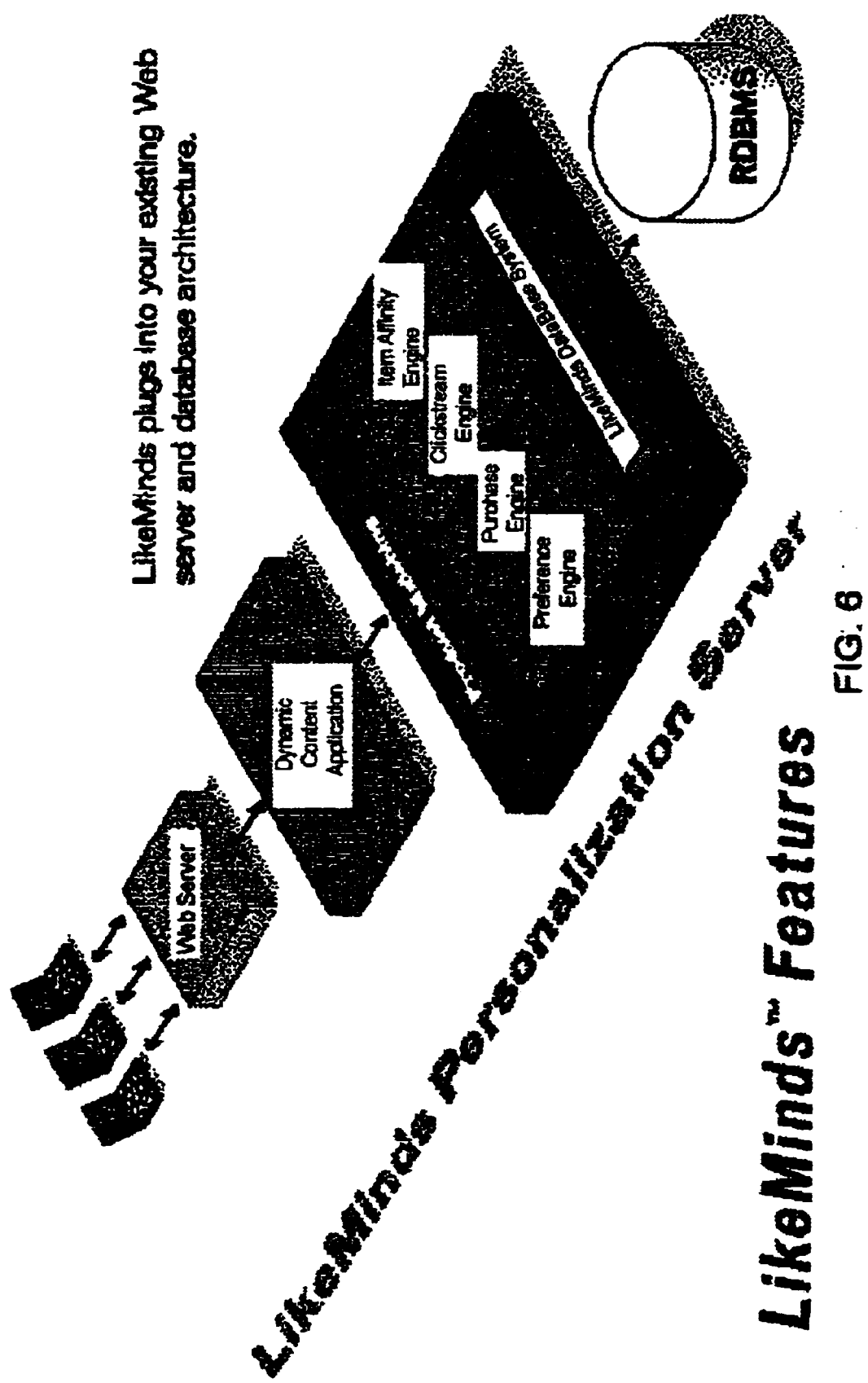
FIG. 6 is a diagram of the Likeminds™ Personalization Architecture which shows personalization occurring apart from the web content manager.

In use according to the present invention, multiplayer neural networks are used to determine the patterns of inputs that are most likely to lead up to a sale. The patterns of inputs are referred to as a behavioral emotional footprint that comprises at least three steps leading up to a sale. U.S. Pat. No. 4,897,811 by Scofield et al describes an N-Dimensional Coulomb Neural Network Which Provides For Cumulative Learning of Internal Representations. For multiplayer neural networks, refer to U.S. Pat. No. 5,822,742 by Alkon— Dynamically-Stable Associative Learning Neural Network System and U.S. Pat. No. 5,119,469 also by Alkon—Neural Network With Weight Adjustment Based On Prior History Of Input Signals. Alkon says in U.S. Pat. No. 5,119,469 in accordance with the present invention, the input presented to a basic neural network architectural unit comprises a first input signal comprising a set of conditioned stimuli (CS), and a second input (UCS) signal comprising an unconditioned stimulus. In some embodiments of the invention, CS arise from a historical pattern to be classified and UCS represents a classification category. Conceptually, note original patent drawing FIG. 4c shown in drawing FIG. 4 shows the flow-through connections are analogues of pathways for unconditioned stimuli (UCS), and the collateral connections are analogues of pathways for conditioned stimuli (CS). The neural networks learn to combine and differentiate in a manner similar to the human brain. Sets of signals representing the exemplary desired (CS) input patterns are successively applied to the primary inputs and propagate through the neural network to the output. The differences between the actual and desired output vales, determined by the external teacher, are calculated to arrive at an error signal that is employed, typically with a nonlinear algorithm, throughout the network to adjust synaptic weights. The synaptic weights are used to adjust the effective value of the various neuron inputs to permit the neural model to be used to predict the behavior of a system that has learned from past behavior. Neural networks are useful for pattern recognition that is associative or content-addressable memory for producing a class exemplar form an input pattern as described by U.S. Pat. No. 5,359,700 Seligson Neural network incorporating difference neurons which actually uses a difference neuron. This process is repeated in a recurring manner and typically requires a large number of iterations to reduce errors appearing at the primary outputs to an acceptable level. This method is referred to as the backpropagation method.

One other well known noniterative method of using a neural network employs Gaussian probability method is discussed by Minot in U.S. Pat. No. No. 5,568,591 which disclosed the use of multiple multilayer perceptions ('MLPs') in a neural network which classifies data vectors using a method that utilizes comparison of differences between authentic specimen signatures known to be from a specific person and unknown signatures not known to be from the same person. Minot method is suited for comparisons where a small number of sample specimens are available. The adaptively trained system employed synaptic coefficients or weights determined by training on the differences between training specimens of a known authentic class, the network being adapted to fit the number of specimens to the classes. A network as trained is capable of verifying signatures by operating rapidly and repeatably using the synaptic weights retrievable from a stored database. The connection weights for input neurons were determined by comparison of input layer neurons and correction neurons calculating a Bayesian and by comprising internal layer neurons and correction neurons and adjusting weights associated therewith. The input layer quadratic neurons 3, internal layer hyperellipsoidal neurons 4 and output layer 5 which gives the probability that signature is in either class 1 (valid). It is not necessary in the case of signature comparison to use a second class of known invalid signatures for comparisons, that being difficult unless samples of invalid signatures are used for training. The input neurons 3 are inter connected with correction neurons 6 and internal layer neurons 7 which are set to −1 compared to weighted inputs for purposes of finding optimal weights Statistical calculation of mathematical relationship of $\Gamma$ (covariance matrices of normal distribution of k samples are the k neighbors) and $\mu$ (centroids of the distributions). Complexity increases as each new difference requires a new internal layer neuron and each new class requires a new output neuron.

In the present invention, the BioNet Method And Personalized Web Content Manager Responsive To Browser Viewers' Psychological Preferences, Behavioral Responses And Physiological Stress Indicators, after training is completed and the neural network controls a network computer system of computer browsers, a trained control program can then combine the multiple inputs make a decision to instruct the network how to behave (what to deliver to the browser) in response to inputs from a browser user who is interacting with the network with or without physiologic input data.

In some cases, the neural network can initiate activity on its; own without real-time input. For example, when a known set of legacy data (psychological characteristics) is associated with a particular product. Inputting the known set of characteristics can be used to determine multiple emotional footprints at several possible states along the progression shown by example in FIG. 8. With knowledge of the emotional footprints, the default or standard campaign can be used in cases where physiologic inputs are not available.

Figure 7:
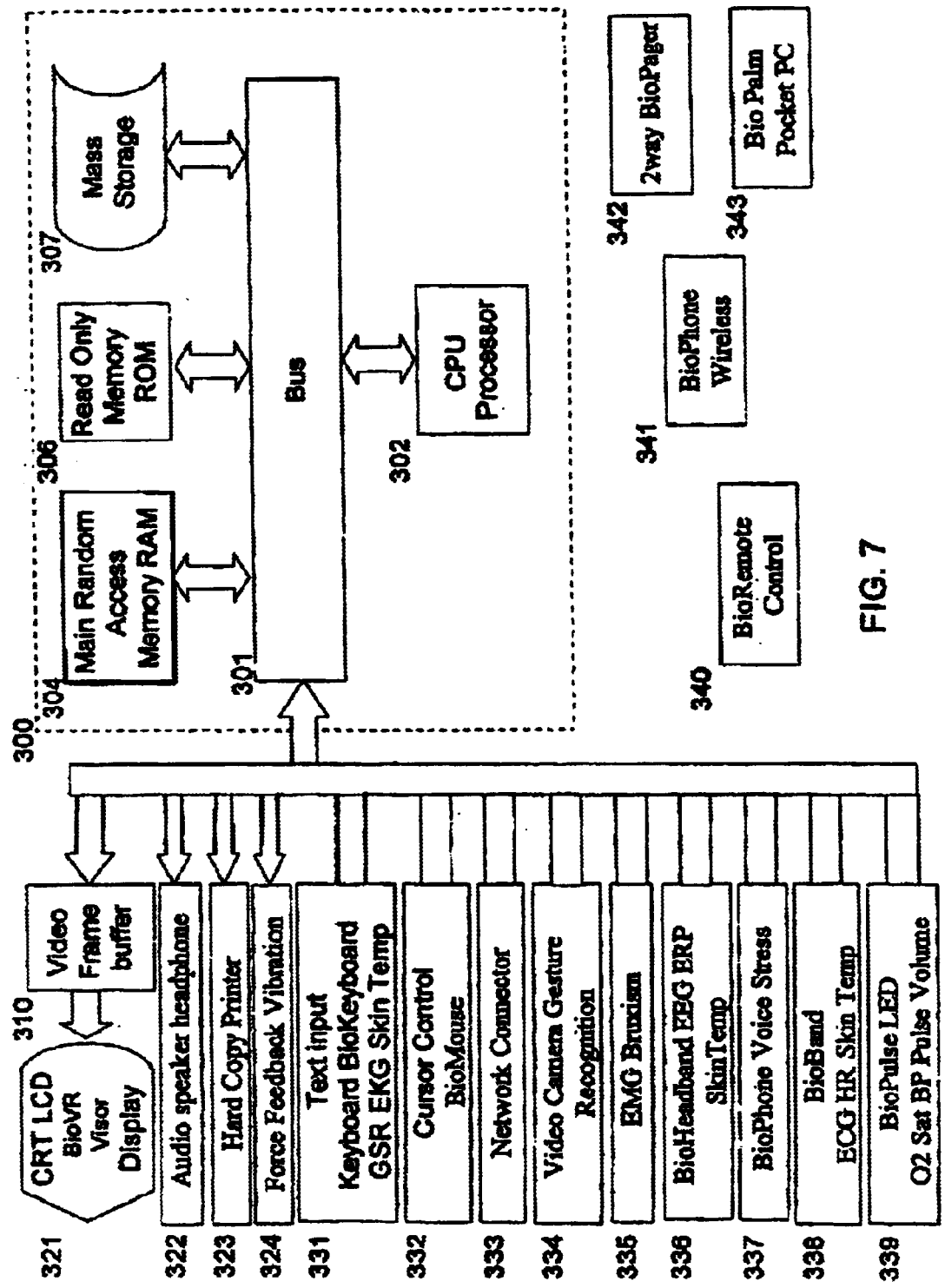
FIG. 7 is a block diagram of a computer system on which a browser or web server may operate, such as a workstation, personal computer, Palm Pilot, Pocket PC, wireless browser or other processing apparatus in which the client 50 or server 150 may be operative.
Figure 8A:
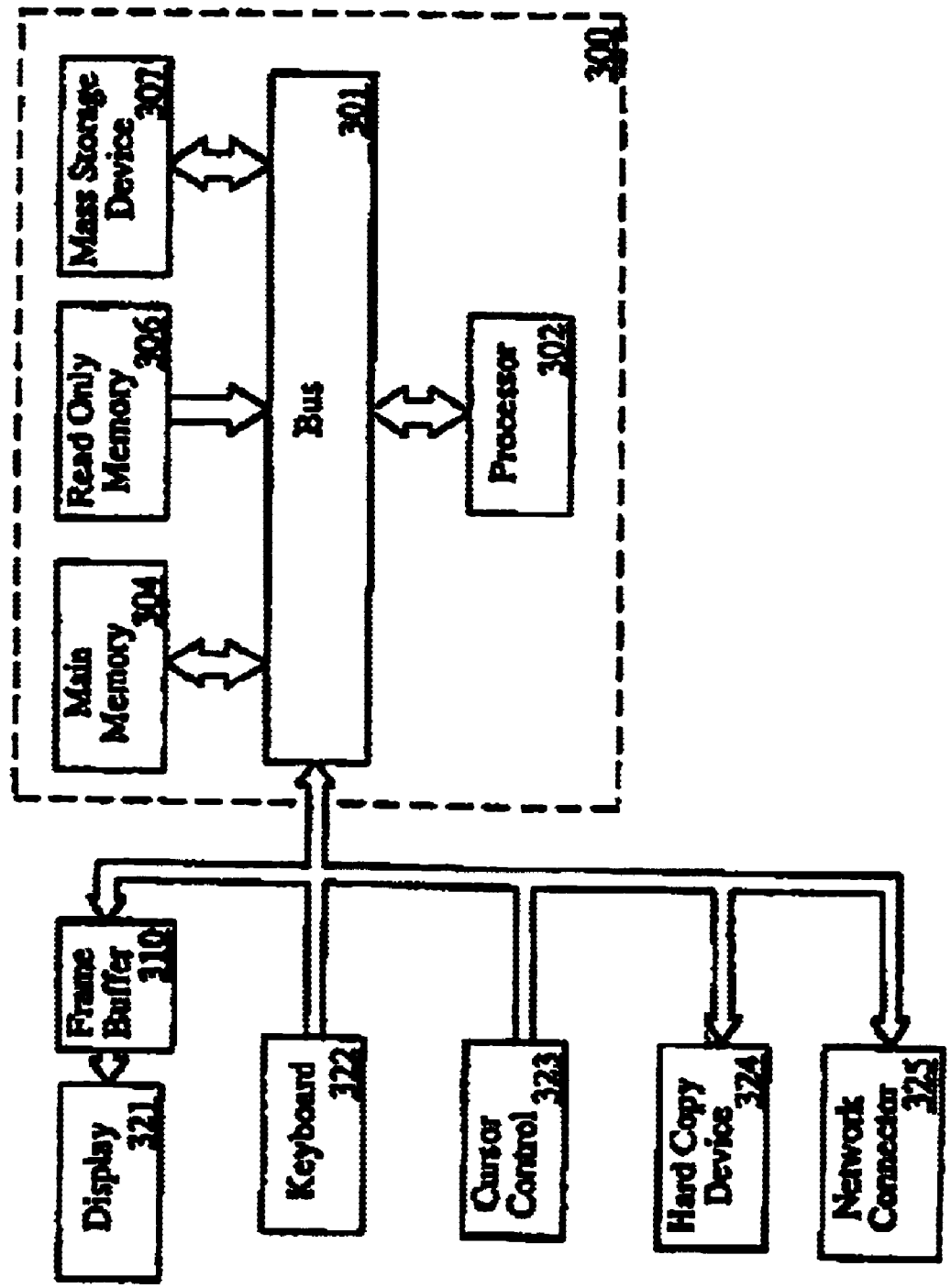
FIG. 8A is a block diagram of computer systems shown in PRIOR ART U.S. Pat. No. 5,784,608.
Figure 11:
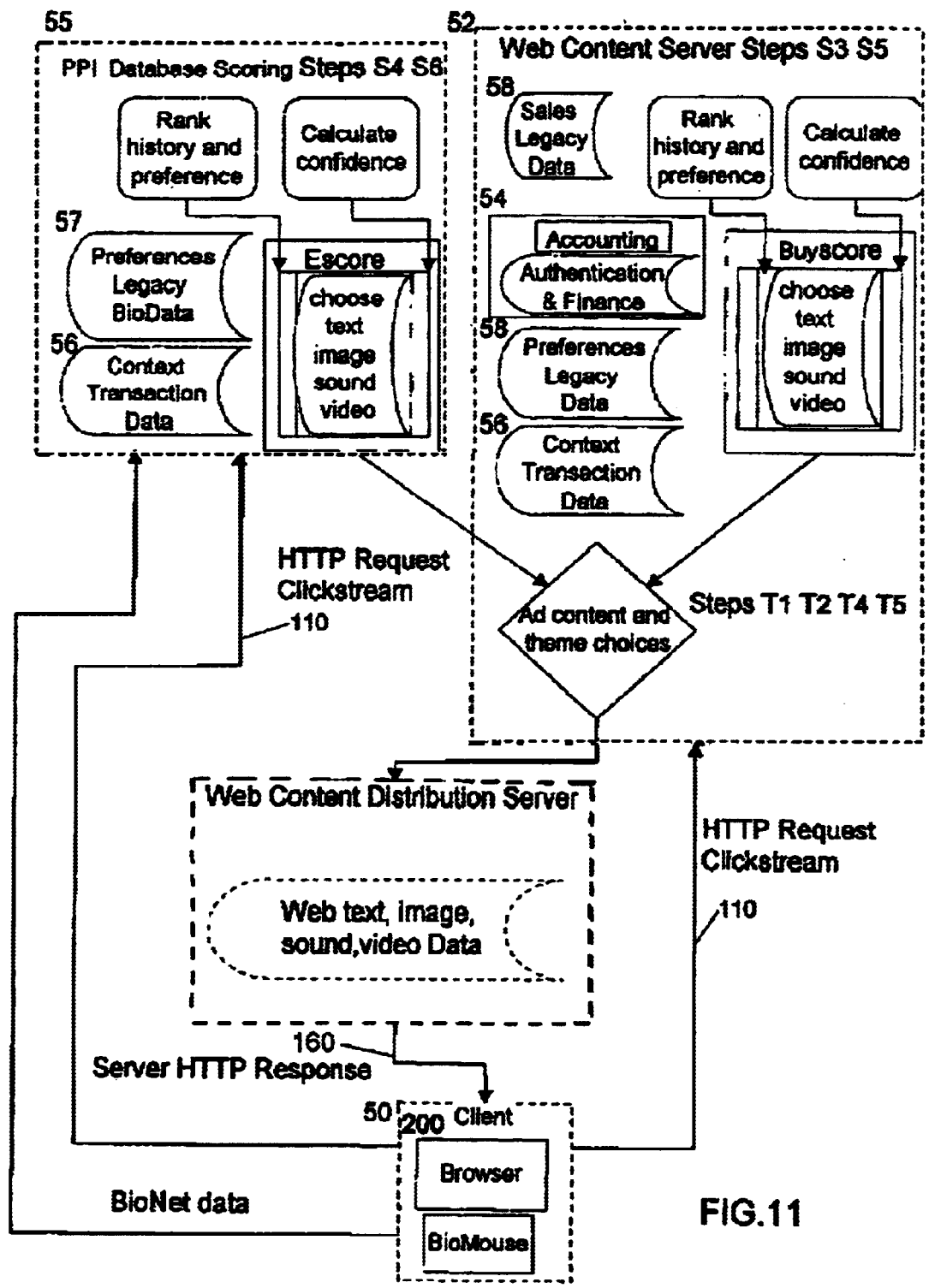
FIG. 11 is network dataflow diagram to and from Web server client, database and financial credit debit server for the BioNet method and personalized web content manager responsive to browser viewers' psychological preferences, behavioral responses and physiological stress indicators.
Figure 12:
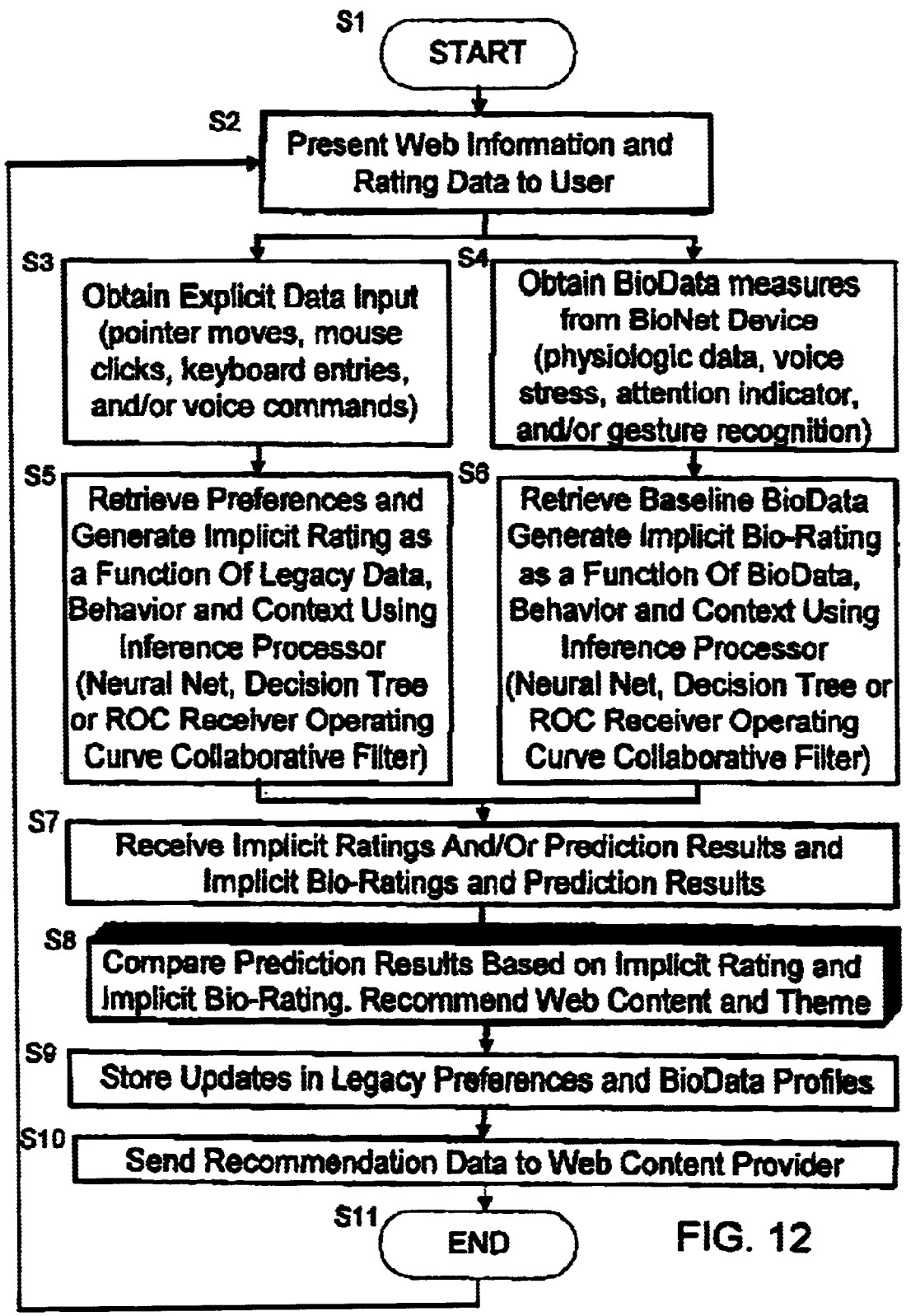
FIG. 12 is a Flow diagram illustration of combination of legacy rating and BioRating shown by parallel processing and comparison of predicted results in compound neural networks. Predictions based on explicit data input, behavior, context and legacy data inputs are compared with predictions based on BioData Behavior and context as employed in a BioNet system and personalized web content manager responsive to browser viewers' psychological preferences, behavioral responses and physiological stress indicators as processed without and with BioData for purposes of suggesting web content and style and updating legacy data preferences and BioData profiles.
Figure 13:
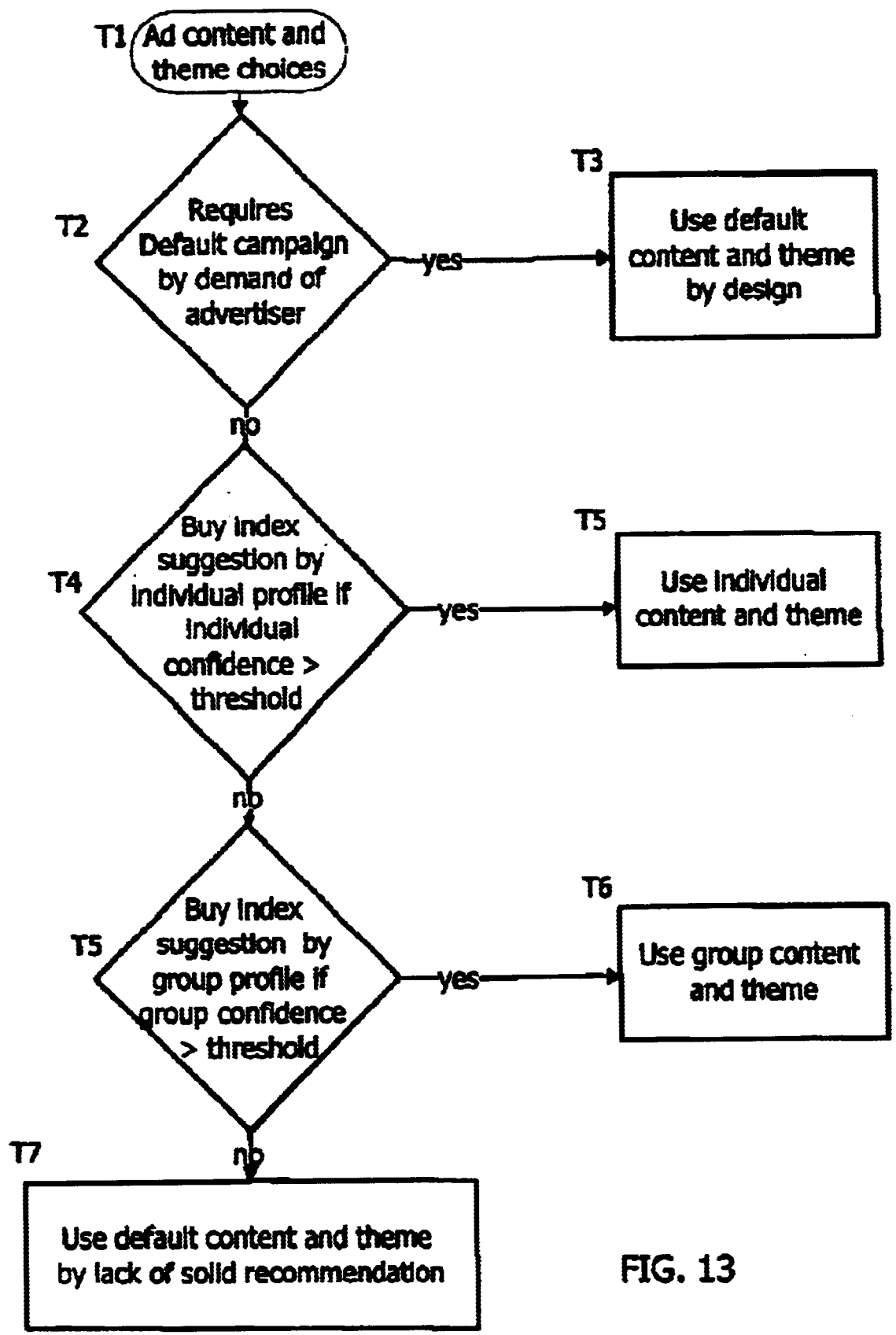
FIG. 13 is a flowchart that shows the logic of selection of the recommendations ad choice using a selection method based override to a default ad campaign for testing T3, based on individual profile recommendation based on individual prediction data above a threshold confidence level T5, or based on group profile recommendation based on group history and prediction data above a group threshold T7 and default ad campaign where confidence does not meet either individual or group threshold levels at tested in steps T2 and T6 and default must be used T8.

FIG. 7 shows a representative database listing of input signals and several psychological and emotional categories that are clustered subsets of signals is that may be accumulated as a cluster score for a characteristic subset of viewer with recorded activities or survey questions that put he browsers viewer into a class describable as assertive, interactive, fearful, greedy, strong locus of internal control (I do it may way"). Thus in accordance with the present invention, the neural network combines characteristics of browser user sessions and legacy data, and physiologic signals to recommend ads media and content themes to able shown to viewer. The weighed outputs called Escores are the equivalent to a score for conditions at that are evaluated in terms of leading a sale.

To reach a minimum core of functionality and to make a simpler explanation, the context of the sale has been divided into three basic categories of pre-purchase condition, the first state being the entrance or first view of a web page and the beginning of the information acquisition, the second state being information gathering up to and after product is selected, and the third being the state after pricing and negotiation of details is completed but before a sale is completed. Knowledge Base creates behavioral emotional footprint that records at least three actions that precede to a sale. There are many pathways to a sale as is illustrated in tree diagram or footprint diagram in FIG. 9. ???????

The knowledge base is created by forming statistically large groups of people, where each group exhibits the same psychological or physiological characteristic. A larger superset of people is divided into these psychologically or physiologically homogeneous groups by conducting a psychological or physiological assessment, respectively, of the superset.

As will become apparent from the description below, the present invention may be adapted to use any website configuration. For convenience, much of the description below concerns psychological/psychological characteristics, although those skilled in the art will recognize that the invention may easily be adapted to measure responses after the database has been created using Biosensors for, acquiring psychological/physiological signals have been removed or the browser is accessed from a location that is not equipped with the necessary equipment.

In the classical null hypothesis test used in "lie detector" analysis of stress a comparison of a normal response at a reference condition and a response known to be made under a condition of falsehood. Regardless of the test employed, formation of the knowledge base requires two basic steps. First, psychologically homogeneous groups are formed based upon a psychological assessment, similar consumers are grouped together. Second, the physiologic and parameters most closely associated with each group are determined. To perform this step, each viewer ("reference subject") in each group responds to ad impressions and has physiologic signals monitored and if present speaks into the microphone of a voice stress analyzer, is observed by the gesture recognition device or physiologic stress monitor. Each viewer's physiologic signals and speech is then parameterized. The process for parameterizing both the reference subjects' speech to create the knowledge base, and the test subject's speech for the later pattern comparison are illustrated in FIG. 3 of U.S. Pat. No. 6,006,188, issued to Bogdashevsky reproduced here as The process for parameterizing the reference subjects physiologic signals GSR in pending "BioMouse" patent application Ser. No. 09/497,096 and in the attached FIG. 15 is FIGS. 1 and 2 from the BioMouse application which is herein incorporated by reference.

None of the earlier patents provides a means to working without prior knowledge a priori collection of data on a new viewer or subject. We recognize that ad servers and web page authors have typical viewer demographic data, and preset static data or personally customized preferred or a preset ad campaign, a program a planned scheme of impressions that is to be shown to every viewer. Physiologic responses and voice signals are acquired in response to impressions and a knowledge base is created.

The prior art U.S. Pat. No. 6,006,188 issued to Bogdashevsky describes a speech-based system for assessing the psychological, physiological, or other characteristics of a test subject. The system included a knowledge base that stores one or more speech models based on a characteristic obtained from a group of reference subjects. Signal processing circuitry compared the test speech parameters of a test subject with the speech models. In one embodiment, each speech model is represented by a statistical time-ordered series of frequency representations of the speech of the reference subjects. The speech model is independent of a priori knowledge of style parameters associated with the voice or speech. The system included speech parameterization circuitry for generating the test parameters in response to the test subject's speech. The speech parameterization circuitry included speech acquisition circuitry, output circuitry for outputting at least one indicator of a characteristic: in response to the comparison performed by the signal processing circuitry. The characteristic may be time-varying, in which case the output circuitry outputs the characteristic in a time-varying manner. The speech characteristics are compared with the Jungian characteristics using the so Called Brigs Myers compatibility profile.

The array of BioNet inputs is H Ps E B C Ph G as shown is figure Table 1. Since the system is learning all signals is done real time these can change. However the history H, Ps psychological, E emotional, and C cognitive aspects are reached through collection of data made available on a legacy database and will require some stability for reliability when used for estimation purposes but allow for change as new experiences and routes are charted.

Indicator sources include H for individual history, Ps for psychological compatibility, B for behavioral "motivators", and E for emotional motivators C is for Cognitive G is for gesture recognition, that are combined as a weighted collection of factors called the Escore. Escore is used to indicate the affinity of a viewer for materials that have been shown and can be an indication of the likelihood of making an order for material or purchasing goods software (computer programs, photographs greeting cards, literature, or reading materials), H individual history included at website, previous web pages viewed link source, number of times viewed, number of links or layers entered, where on hierarchies present context (state 1 introductory viewing 2 information gathering or 3 end stage loading shopping basket) in the prebuying stages), past purchases made, and stated viewer preferences personal profiles or commonly assigned profiles built using demographics of like consumers of the particular product if no profile is available.

Ps psychological compatibility indexes Myers-Briggs Jungian character types. Character types are chosen from combinations of four sets of opposite character constructs, E-I (extrovert-introvert), S-N (sensoric-intuitive), T-F (thoughtful-feeling), J-P (decision maker-plagued).

In category B, behavioral "motivators" are baseline customers for web page authors, membership in knowledge base "like groups", portal membership surveys and past activity history. In category E, emotional motivators one may use a checklist from Mazlow's hierarchy of needs such as Security vs Fear, anxiety and loss; self confidence vs doubt, trust in others, Faith congruence with values ideals or identity with persons or points of view, greed, envy, guilt, loyalty or personal involvement: affinity and ownership versus isolation and keeping at a distance, aggressive/assertive and passive/interactive styles and various permutations of the above.

Further pattern recognition may be optimized after physiologic signals that indicate anger or fear may trigger a review of historical data to identify the specific types of anger and fear which should be recognized, categorized and used for prompting the appropriate theme and content. Physical signs of anger include increased hear rate and blood pressure. Trembling speaking voice and poor posture are indicators of fear. The most common types of fear found in negotiations fear of failure, loss and the unknown and lesser fears of humiliation and suffering. The context of the situation will be a cue that indicates the kind of fear and processing the cue will allow the appropriate web content prompt to be recommended and used as hereinafter described with reference to FIG. 10.

C for cognitive baseline customer demographic is derived from individual legacy data, web page collaborative filtered demographics (most users who view this page have similar opinion surveys, past activity history and legacy data), or simply what is expected by the ad campaign manager for all consumers who reach the page. cognitive baseline customer data is an approximation or prediction of what the what the consumer thinks she or he is going. This includes locus of control that is who is leading whom and who is planning the next move among other factors.

Ph is for physiologic signals, EEG electro encephalogram (ranging from simple band pass filtered power density correlations) and blink detection the greater the number of blinks per minute the higher the anxiety, sophisticated analysis of ERP (evoked response potentials) to indicate attention or discomfort, GSR galvanic skin resistance (that indicates sweaty palms), skin temperature, pupil dilation, voice stress (changes in spectrum of speech), respiration rate by thermistor or hotwire anemometer flow sensor or transthoracic (across the chest or arm to arm) impedance, hear rate by blood pulse detection via infrared diode or EKG electrocardiogram.

G is for gesture recognition accomplished by computer analyses of video inputs. The position of the face as recognized by analysis of processed video signals indicates an upbeat or downbeat attitude. The count of blinks per minute may be used for indicating anxiety. The closed facing to the side or open facing the camera view of interactions made when facing an avatar, a human like interface that looks and speaks as if a human being were a talking head on the computer screen may offer the closest clues to viewer attitudes that can get closer to the information obtained by direct face to face observation of a viewer. The method of neural network pattern recognitions and analysis of pathways leading up to a sale is presented in the flowchart FIG. 12.

Observation of pathways taken will provide a working example as shown in the bracket diagram on FIG. 10. With reference to the drawings a scenario shows and example of two persons, John and Joe, both of which have with known database or pre-survey information to have a high level of assertiveness on an assertive interactive/scale. Two individuals received different web site treatment according to recommendations based on the combination of additional legacy variables depending upon the known degree of internal/external control. The example shows John, who has a high level of internal control who remains in control of negotiations, and Joe whose internal control level is lower and may be led or pushed by prompts of fear or guilt by the sales agent. The following simplified two scenario example works using the legacy database information for more accurate personalization and prediction for the known non-anonymous with a psychological profile that can be used and proposed media and thematic choices determined more rapidly and accurately than anonymous users. Anonymous users may still be tracked based on IP address for each session tracking to establish useful predictive suggestions based on broad demographics, click stream and physiologic responses that identify the traits of a demographic group. Neural networking or collaborative filtering observation of trends for physiologic reactions correlated with a group that has the higher degree of internal control may be used to suggest media and themes appropriate for the group even without the personal legacy data. Multiple kinds of predicative models may be used for finding rules and making predictions. Neural networks are preferred based on fast learning characteristics. However, Linear regression, Logistic regression, collaborative filtering (clustering/filtering), and decision trees may be used for finding rules and making predictions.

In a first scenario that utilizes legacy psychological/physiological profile with decision trees and BioNet signal monitoring is described with reference to FIG. 10. Behavioral Prompt after a score that measures high Assertive & Interactive, all the way through to the Sale. Beginning at the START BOX, John logs On to Packard Motors Home Page. Two sales tracks are described according to a simple decision tree based on different levels of internal/external control. In the on the left hand side of the figure Internal control is high and remains high, in the control of the consumer. The eScore profile notes John has a desire to be assertive and choose the media choice is "when assertive interactive threshold is reached chosen media is designed to meet consumer 's content desire with a theme that suites the consumers self determination personality." System is recording and responding with recommendation based on the real time user responses clickstream browser activity and physiologic signals that indicate acceptance or rejection of media prompts. Profile (legacy data) and context are used to select follow-up media prompts and content themes in response to physiologic and viewer reactions (browser activities) observed by the system.

A1 Cognitive Prompt (Internal Control)

High threshold eScore is reached for internal control. At this point John, the consumer, takes charge of choices from web vendor. John sees his options as the master of his own fate "Heads I win tails you lose. Now you pick one." Collaborative filter or neural network memory of the historic behavior of other persons with high internal control scorers suggests the name your own price option.

A2 Cognitive Prompt (Expectation is to Name Your Price)

High threshold John accepts invitation to guess our invoice cost. Cost is disclosed with an invitation for John to offer an amount to, pay above invoice. The counter offering a price may use excess inventory price bidding systems like priceline.com ubid.com and other bidding websites that auction or choose a price based on offer and acceptance for individual or grouped bids. The on line exchange of an offer and reviewing the offer is the equivalent to a visit to the manager's office for price or bid approval. This process resembles in-store price haggling or bantering that involves getting the manager approval of a minimum acceptable price for a dealer. Preliminary physiologic indicators of viewer response are helpful inputs to assist the price selection system in assessing viewer response. Physiologic indicators of high stress and interest/disinterest that could be considered the equivalent to a shrug, a blank stare, a toss of the head or head shaking signs that a live exchange would provide a cue to the sales person to revisit benefits or add factors to reinforce consumer's desire to buy. Psychological/Physiological signals are stable, showing no perturbation, no discomfort or stress. In other words, customer's voice does not crack under the strain of negotiation.

A3 Emotional Prompt (Greed)

High threshold is reached. John is a discount guy shown in his legacy profile. Neural data and collaborative data suggest this is the time to deal. He wants the bargain sale price. Give him what he wants.

A4 Emotional Prompt (Anxiety) after Best Price & NO SALE

The competitive price offered is as low as retailer will go. System can make no further price drop. But there is no acceptance yet. Biased again on neural net data, collaborative filters for the greedy profile and neural networks logistic regression an emotional hang-up anxiety is indicated as possible. Suggested response is a 30 day price guarantee that reassures that no better deal can be found and resolves the fear of losing a better deal.

A5 Behavioral Prompt (Passive Avoidance)

John likes guarantee but still won't buy. Neural net response is based on behavioral history using legacy data that confirms this is John's emotional footprint. He is avoiding a fear that the purchase represents.

A6 Emotional Prompt (Fear of Failure)

John likes the deal and the retailer but is afraid to screw up. John's behavior is frozen perhaps obsessed subconsciously. Neural filter suggested response is a Trust probe. Have we given you what you asked for?

A7 Cognitive Prompt (Trust)

Relationship including Trust element is sold to John. Believe in us we won't let you down. Physiologic signals still indicate stress as John keeps this trust in his back pocket as excuse if decision to buy was wrong. John won't be responsible for a failure because he puts his faith in the retailer.

Special eScore is an abbreviated identifier for a special consumer category, in this case High Internal Control &Trust is noted after SALE. The special eScores may be stored locally on consumer's machine via cookies or in a database linked to the consumer's identity on the web server or on the PPI database to assist web vendors by rapidly noting a membership in a special customer category.

John believes sale was his choice and not reaction to sales. John gets car that he was looking for AND holds the belief that his actions were of choice rather than reaction. The fact that John needs independent choice and the trust element that takes him off the hook is noted on his personal weighted eScores and may be stored locally in a browser cookie and on a centrally stored eScore in a PPI database. At a minimum the emotional footprint for last three links traversed and associated themes "Fear of Failure" "trust" are added to John's legacy profile.

In a second scenario discussed with reference to FIG. 10, Joe logs on to Packard Motors Home Page. The path is shown beginning at the START BOX. He views various autos and selects one at box A1. Based on previous survey information obtained before logging on to this website various scores have already been established including activated cells Assertive, Interactive, Greed, Fear of losing the deal. From Joe's various activated cells we his general modus operandi or behavior is assertive interactive (as opposed to passive/aggressive, passive/avoidance). Joe has responded with a high assertive/interactive score when polled on his opinion about salesmen and various styles thereof. In contrast with the example above Joes locus of control allows Joe to follow the lead of a sales person.

B1 Cognitive Prompt (External Controls)

Joe is assertive in researching and choosing the retailer who he is confident will be able to fulfill his need. However, once chosen, Joe wishes to believe the experts that he has chosen, "know best." Joe relinquishes responsibility of determining what is best for him not what choice to make once a determination has been made. He switches to external control after the choice of vendor is made.

B2 Cognitive Prompt (Assumptions and Ideals)

Joe assumes the unsolicited $2000 discount off the MSRP list price is a result of honorable and generally "no haggle" policy promoted by the car dealer. Joe scores high on Assumptions and Ideals about himself and therefore is viewed as likely to expect similar deals from others with whom he interacts. Joe's psychological/physiological signals show no stress.

B3 Emotional Prompt (Guilt)

Joe is strong-armed with guilt prompt reminding him he came to us for a reason—we made choices based on what you requested and in your best interest. We didn't beat you up while you got your discount. Thus, Joe is browbeaten to uphold his part of the deal.

B4 Emotional Prompt (Fear)

Joe is reminded how intimidating other car dealers can be when he is pressured to choose and negotiate for himself. Joe's psychological/physiological signals show stress.

B5 Behavioral Prompt (Passive Aggressive)

Joe likes to deal offered and really does not want to go elsewhere, but still will not buy. Joe wants to buy but has lost face when brow beaten. Joe's psychological/physiological signals show increased stress, by voice stress increase, heart rate increase, head shaking no (gesture recognition).

B6 Emotional Prompt (Anger)

Joe feels angry. He feels fear when car shopping and now holds out and "cuts off his nose to spite his face" even when a good deal is offered.

B7 Prompt (Ideals/Identity)

Joe is reminded he is a special and respected customer whom the president of the company would like to personally like to contact him and thank him for his confidence. A sale is made.

The pattern of increased stress after negotiated sale price is a low pressure push sales technique. This specific response may be used only when the preceding flowchart schematic is present and the "key customer" sale would produce large income figures. The last three steps fear prompt, anger relief prompt ant appeal to ideals and vendor identity is recorded in Joe's person al history.

A2 Special eScore High Internal Control after DIRECT SALE

If a sale is made at #A2 via direct path A1 to A2 the eScore system would record the sale pathway and interpret the sale to be a related to the High Internal Control for the individual and the group of similar consumers identified by collaborative filtering. PPI database correlation would give both the individual and a filtered group a higher E-score result that indicates the closeness to the final step on a pathway that is successful for an individual.

The system must be able to work when insufficient information is available. A higher E-score is associated with the pathway that succeeds in making a sale. However when the default website recommendation of a content theme is overriding that is able to use default selections for trial and error approaches and is also aware of failure to make a sale: and updates are made to individual profile accordingly. As is noted below the pathways that available are unlimited. The system may suggest a move to an entirely different pathway based on knowledge that the alternate path may be fruitful.

Traversal to Alternative Presale pathway is noted in the eScore data base. For example if the sale occurs via above pathway two steps A1 to A2 is and is correlated closely to other sales that have occurred via 5 steps, B1A1 To B1B1 to B1B1 to B1B1A1 to B1B1B1, said correlations may be used to channel users through the filter. If no sale was made at A2 and the system later filters the user to A2A1, the system may cross over to point B1A1 prompt and progress accordingly from that point according to a preferred pathway. The eScore index is higher that individual and suggests media type and content themes on the B1A1.

The system continuously refreshes the eScore at every point traversed on the matrix according to what route and how many steps were taken to get to a particular point in the matrix. The database may be maintained that establishes the shortest pathway (most proficient means) for pushing a user from one location in the matrix to another given point. The database may be maintained that establishes the greatest historical likelihood of successful sale. The individual's historical sales record indicates the pathway that succeeded in the past. The choice of best pathway may be made by comparison of an eScore (likelihood of successful sale) for each optional pathway. The system can then make available suitable media in any of several methods pop ups, ad banners, message suggestions, follow-up by postal mail, electronic mail, telephone call. Vendor cooperation is needed to make the database for external follow-up.

Override scenario details for tool buyer entering website with fixed promotional plan. At A2B1 by response to a web picture ad for a power wrench from Sears where there is no name your price option here price is named. The progression of pages shows A1 B1 opening screen with models available and pricing. Offer to join affiliate program to get special, discounts is made at A1B2. Viewer acceptance of offer to join affiliate program gives access to limited time offers, specials and promotions. Display of product are synchronized monitoring of psychological/physiological stress/interest indicates some varying level of excitement in individual products. The psychological/physiological response monitoring confirms interests that have been profiled in the surveys and suggests other products that have increased the consumer's interest. Profile is updated with content information from physiological/psychological survey that is part of the questionnaire for joining the affiliate program. Click-through behavior (joining the affiliates for discounts) modified to the greed index. Suggests web themes will focus on greed prompts on the items that have been indicated to be of interest by survey and A1B2B2 lead to a sale or blank box indicating another other chosen media email with price drop reminder and viewers indicates going to browse on another subject.

Key buying history indicators (kept by website) include: total amount of purchases, total amount returned or cancelled, average number of items per order, days since last order-recency, current back order dollars, purchasing cycle stage ($1^{st}$ first ad viewing, $2^{nd}$ probing for configuration or sizing and detailed price information, to shopping done choosing shipping and $3^{rd}$ payment method, and post sale delivery return which is first ad viewing), number of times ad is viewed, status active customer old or new (noted by first purchase date), number of purchases in recent 6 months, average frequency of visits per month, average frequency of buys per month, last purchase date, total net profit, total sales revenue, product categories purchased, total gross profit, purchase type (first, repeat, multi-repeat), returned dollars. These data points are analyzed in combination with Biodata (physiologic signals and gesture data) via a neural network to obtain select the best media choice in terms of content, mood and theme rather than content alone. Monitoring Physiologic signals may provide some reporting means to the advertisers for evaluation of ad campaigns showing the effects of ads on consumers even before viewer sales decisions have occurred.

In summary, the client connection with a browser viewer communicating via IP packets to a server may operate in a variety, of physical devices. A physiologic monitor is connected to the PC by hardware means selected from the choices bi-directional parallel port, USB (universal serial bus), serial COMM port, IEEE 1394 firewire port, iRDA infrared port, and wireless Bluetooth data connection, which communicates physiologic information via Internet Protocol to a server. A physiologic monitor may be a browser on a Web TV or satellite TV with hand held remote that uses a built in physiologic monitor and wireless communication channel for connection to a server via IP communication means. A Pocket PC or Palm-Pilot (R) personal digital assistant ("pda") uses a connection to PCMCIA or compact flash data port for collateral connection to a physiologic monitor. When a user logs into a web browser a first physiologic parameter baseline is established at a client connection, a computer browser viewer and input device with physiologic monitor and transmitted via IP to a server. When a user clicks on a banner advertisement or otherwise begins to view ad content, an impression is established, the impression start time is stored, the user's identification and second physiologic baseline is recorded. Later, when the user undertakes post-impression transactional activity such as downloading software related to the impression, ordering products: and services related to the advertisement, and so on, the transactional 'activity along with the user's identification, time after impression start time and physiologic parameter changes from baselines are recorded. Stored, data at a tertiary central psychological server indicates the cumulative number of times this individual has viewed the media (ad content), the duration of views and results in terms of behaviors and physiologic responses to impressions to arrive a PPI physiologic profile indicator.

Independent of content, media is categorized according to media type for example "text only", "highlighted text", "animated text", "spoken verbal audio", "musical jingle", "music only not words", "short video only animation up to 5 seconds (animated gif)", "audio (music or voice) over short animation", "audio video segment of a variety short (up to 10 second), medium (10 to 45 second), and standard (45 seconds to 120 second) and long (more than)", online seminar "real audio windows media player programs", web call offer (click to have sales person call pre-stored phone number immediately or at a preferred time).

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A method for handling ad media transfer between a network and a user browser, comprising:

i) receiving a network request from a user input device (PC keyboard TV remote, cell phone with physiologic sensors) for first network information (ad), wherein said receiving includes capturing time of request, baseline physiologic network information (temp GSR heart rate EEG), start time of ad, the type of user request from the user input device including the user request on the same user input device or a second user device (TV PC screen cell phone display);

ii) receiving a second user request (sale order, request for information by mail, click through for additional information, moving to other display ads or content); from a first user device; wherein said receiving includes capturing a secondary physiologic network information sample2 (temp GSR heart rate EEG) as a physiologic change from baseline observed in the two time intervals 15 seconds and the last 25% of time from start of ad from start of ad to the response for a single user regarding the user request from the first user device and the display user request on a second user device (TV PC screen cell phone display);

iii) retrieving baseline physiologic network information;

iv) processing the baseline physiologic network information and secondary physiologic network information to derive a media preference comprising a weighted score based upon the type of second user request (using greater weight for final sale, lesser weight for a request for information by mail, lesser still for click through for added information, and no credit or negative credit for moving to other media);

v) transmitting said media preference information over a communications media; and vi) receiving said media preference information and composing secondary information based on current viewing status with regard to prepurchase phases, phase 1 browsing, phase 2 hunting for a product or reading other materials, and phase 3 product selected and ready to buy, recorded media choice, demographic, user interest and product preferences for display in a second instance on the second user device (TV PC screen cell phone display);

vii) using said media preference information to chose the preferred media and content theme for use for the user.

2. A personalized web content manager for controlling web content viewed by a consumer, said consumer having personal preference, based on a legacy knowledge base survey and an behavioral and emotional response foot print verified by real time physiologic-psychological input combined into an Escore for predicting the most satisfying consumer choice comprising a) a set of questions for presenting to the customer set of questions that determines basic psychological profile that identifies at least a four component personality profile, b) a set of action for responding to initial inputs to, c) a first set of rules governing selection of media by the web site provider that chooses content and theme for web pages, based on standard ad campaign information, d) a second set of rules suggesting the preferred media choice bases upon historical choices of individual consumers in that category of goods, e) a third set of rules suggesting preferred thematic choice based on historical choices of consumers of like sentiment based upon filtering of consumers of similar psychological profile, using physiologic and behavioral data to confirms choices of consumer before click-through occurs;

f) an input means for receiving physiologic stress indication, g) a storage means for recording a behavioral and emotional footprint comprised of a set of physiologic stress indications and consumer behaviors that occur as web pages are viewed, h) a set of actions for displaying media to the consumer, the set of actions having a changeable order, i) a decision engine that computes a weighted ratings list of media choices as an E-score that indicates relative progression toward steps leading up to a sale of a to the individual measured based upon weighted components: the physiologic stress indications, the psychological profile, the first set of rules, the second set of rules, and the third set of rules, and the behavioral and the emotional footprint;

j) a website content designer, for automatically generating and organizing said sets of rules, media choices, behavioral and emotional footprints, and informational messages sent through content generation suggestions sent to websites content managers;

k) a detection engine for receiving responses from the customer to said media displays and questions sensing the physiologic stress indicators of the consumer and behavior patterns of the customer, said detection engine having an output, said detection engine operative to:
  (i) applying said second set of rules to determine the respective orders of said media displays, and said questions;
  (ii) processing said third set of rules according to said logical operators when sufficient info about individual is available;
  (iii) receiving behavioral data about the customer;
  (iv) receiving physiologic stress indication from the consumer
  (v) activating decision engine, determining whether said behavioral and physiologic data is sufficient to prove at least one rule of said third set of rules;
  (vi) selecting and initiating an action from said set of actions; and l) an alternative-offering mechanism for offering alternatives to the website that displays for the customer, said alternative-offering mechanism operative to applying said second set of rules to determine the respective orders of said media choices, said, themes, and said informational messages; and further comprising a media selection engine unit operative to:
  (i) processing said first set of rules according to said logical operators;
  (ii) processing said second set of rules according to said logical operators;
  (iii) receiving said responses from the customer and determining whether said responses from the customer are sufficient to prove a rule of said first set of rules;
  (iv) selecting a media choice from the available to recommend to the website
  (v) selecting theme from said set of themes for presenting to the customer;
  (vi) selecting an emotional footprint based upon the category of goods offered on the web page;
  (vii) selecting an informational message from said set of informational messages for presenting to the customer;
  (viii) selecting a closest rule from said third set of rules;
  (ix) determining if said closest rule from said third set of rules can be proven to an individual threshold of consistency by responses from the customer, and if so, presenting the customer with a media content and theme associated with said closest rule in the third set of rules, and if not, exempting said third set of rules and determining if a next closest rule can be selected from said second set of rules proven to a clustered group threshold of consistency by comparing individual responses to the legacy knowledge database, and if said closest rule can be proven by responses from the legacy knowledge database, presenting the customer with media content and theme associated with said closest rule in the second set of rules and if not, exempting said closest rule from the second set of rules, and presenting the consumer with media content and theme selected from the standard ad campaign from said first set of rules.

3. A personalized web content manager as recited in claim 2 for controlling web content viewed by a consumer, said consumer having personal preference, based on a knowledge base survey based and an behavioral and emotional response foot print verified by real time physiologic-psychological input combined into an Escore for predicting the most satisfying consumer choice, wherein
  the storage means for recording a behavioral and emotional footprint comprised of a set of physiologic stress indication and consumer behaviors that occur as web pages are viewed, storing at least the last three steps before a sale is completed.

4. A personalized web content manager as recited in claim 2 for controlling web content viewed by a consumer, said consumer having personal preference, based on a knowledge base survey based and an behavioral and emotional response foot print verified by real time physiologic-psychological input combined into an Escore for predicting the most satisfying consumer choice wherein
  the input means for receiving physiologic stress indication is provided by at least one method chosen from the group of voice stress analyzer, GSR—galvanic skin resistance, EMG—electromyogram, skin temperature, EKG, heart rate, respiration rate, pulse plethysmograph, LED diode pulse monitor, and oxygen saturation O2SAT, iris diameter monitor, and gesture recognition.

5. A network-based sales system, comprising:
a) at least one buyer computer for operation by a user desiring to buy a product;
b) at least one merchant computer;
c) at least one payment computer;
d) at least one psychological profile computer;
said buyer computer, said merchant computer, said payment computer and said psychological profile computer being interconnected by a computer network;
said buyer computer being programmed to receive a user request for purchasing a product, and to cause a payment (purchase completed) message to be sent to said psychological profile computer that comprises a product identifier identifying said product; said buyer computer also receiving media information (ads) and ad type codes
said psychological profile computer being programmed to receive said payment message, to cause an "success" access message to be created that comprises said product identifier and an media success access message including at least the ad type code and authenticator based on a media type sent in the time period before the successful sale, and to cause said "success" access message to be sent to said merchant computer; and
said merchant computer being programmed to receive said "success" access message, to verify said access message authenticator to ensure that said access message authenticator was created using said cryptographic key, and to cause said product to be sent to said user desiring to buy said product.

6. A system for surveying and identifying a psychological user preferences in a personalized web browser using a packet switched transmission in which a plurality of media display types are transmitted based upon media preferences from surveys, said a system having a consumer stress transmission means for recording indices of physiologic responses to said media packets from a website or portal, said websites receiving packet transmission from said user being separately defined from the standard browser input responses, said system comprising:
(a) a digital computer with a database of individual psychological response data organized for selection of media to meet predisposition and sales preferences of an individual based on surveys and filtered data gathered from like individuals;
(b) a physiologic signal detector for sending responses to said packet transmission and detecting said predetermined signal in said transmission based on specific location and timing; and
(c) a controller operatively connected to said detector for causing said detector to detect said predetermined signal based on specific location and timing, said controller being programmed with varying timing pattern of said signal.

7. A personalized web content manager for controlling web content viewed by a consumer, said consumer having an ability to clickthrough to other sites and having a personal preference stored in a knowledge base comprised of survey and emotional response foot prints of past behavior verified by real time physiologic-psychological input before clickthrough action combined into an Escore database for predicting the most satisfying consumer choice comprising
a) an input means for receiving physiologic stress indication by at least one method chosen from the group of voice stress analyzer, GSR (galvanic skin resistance), EMG (electromyogram), skin temperature, EEG Electroencephalogram ERP Evoked Potential EKG (electrocardiogram heart rate), respiration monitor (pneumoplethysmograph or flow sensor), pulse plethysmograph, (fiberoptic or LED diode pulse monitor and oxygen saturation O2SAT), iris diameter, and gesture recognition,
b) a set of questions for presenting to the customer set of questions that determines basic psychological profile that identifies at least a four component compatibility profile,
c) a set of action for responding to initial inputs to,
d) a first set of rules governing selection of media by the web site provider that chooses content and theme for web pages based upon products and standard ad campaigns based on products offered,
e) a second set of rules suggesting the preferred media choice bases on historical choices of consumers of like sentiment utilizing filtering to identify choices of consumers of similar psychological profile,
f) a third set of rules suggesting preferred media choice based upon historical choices of individual consumer and the associated emotional response footprint which includes choices indicated by physiologic responses prior to clickthrough;
h) a set of actions for helping the consumer, the set of actions having a changeable order,
i) a decision engine that completes a rating of the action choices as a weighted E-score that indicates the relative probability of a sale to the individual based on said psychological profile, historical choices, and emotional footprints expressed in the first set of rules, the second set of rules, and the third set of rules,
j) a website content designer, for automatically generating and organizing said sets of rules, questions, comments, and informational messages and sending content and theme suggestions sent to website(s);
k) a detection engine for receiving responses from the customer to said questions and sensing the physiologic stress indicators of the consumer and behavior patterns of the customer, said detection engine having an output, said detection engine operative to:
  (i) applying said second set of rules to determine the first proposed respective orders of said questions, said comments, and said informational messages;
  (ii) processing said third set of rules according to said logical operators when sufficient info about individual is available to determine the second proposed respective order of said questions, said comments, and said informational messages;
  (iii) receiving behavioral data about the customer;
  (iv) determining whether said behavioral data is sufficient to prove at least one rule of said third set of rules;
  (v) selecting and initiating an action from said set of actions; and
  (vi) activating a sales engine unit, an alternative-offering mechanism for offering alternatives to the customer, said alternative-offering mechanism operative to:
  (b) applying said third set of rules to determine the respective orders of said questions, said comments, and said informational messages; and
  (c) processing said first set of rules according to said logical operators;
  (d) processing said second set of rules according to said logical operators;

(e) selecting a question from said set of questions for presenting to the customer;
(f) selecting a an emotional footprint based upon a category of goods offered on the web page; and
(g) selecting an informational message from said set of informational messages for designated to fit the emotional footprint presenting to the customer;
(h) selecting a closest rule from said third set of rules;
(i) determining if said closest rule in the third set of rules can be proven by responses from the customer reaching an individual threshold of consistency, and if so, presenting the customer with media content and theme associated with said closest rule in the third set of rules, and if not, exempting said closest rule from said third set of rules and determining if a next closest rule can reach an individual threshold of consistency and be selected from said third set of rules; and
(j) selecting a closest rule from said second set of rules when no third set of rules can be proven to a group threshold of consistency;
(k) selecting a rule from said first set of rules when no second set of rules can be proven to a group threshold of consistency.

8. A system for surveying and identifying a psychological user preferences in a personalized web browser using a packet switched transmission in which a plurality of media display types are transmitted based upon media preferences from surveys, said a system having a consumer stress transmission means for recording indices of physiological responses to said media packets from a website or portal, said websites receiving packet transmission from said user being separately defined from the standard website responses, said system comprising:
(a) a digital computer with a database of individual psychological response data organized for selection of media to meet predisposition and sales preferences of an individual based on surveys, collaborative filtered data gathered from like individuals;
(b) a physiological signal detector for sending responses to said packet transmission and detecting said predetermined signal in said transmission based on a specific location; and
(c) a controller operatively connected to said detector for causing said detector to detect said predetermined signal based a specific location said controller being programmed with the varying location pattern of said signal.

9. A system for surveying and identifying a psychological user preferences in a personalized web browser using a packet switched transmission in which a plurality of media display types are transmitted based upon media preferences from surveys, said a system having a consumer stress transmission means for recording indices of physiological responses to said media packets from a website or portal, said websites receiving packet transmission from said user being separately defined from the standard website responses, said system comprising:
(a) a digital computer with a database of individual psychological response data organized for selection of media to meet predisposition and sales preferences of an individual based on surveys, collaborative filtered data gathered from like individuals;
(b) a physiological signal detector for sending responses to said packet transmission and detecting said predetermined signal in said transmission based on a specific time; and
(c) a controller operatively connected to said detector for causing said detector to detect said predetermined signal based a specific location or time, said controller being programmed with the varying timing pattern of said signal.

* * * * *